United States Patent [19]
Niedospial, Jr.

[11] Patent Number: 6,039,718
[45] Date of Patent: Mar. 21, 2000

[54] MULTIPLE USE UNIVERSAL CONNECTOR

[75] Inventor: John J. Niedospial, Jr., Burlington, N.J.

[73] Assignee: Bracco Research USA, Princeton, N.J.

[21] Appl. No.: 09/246,798

[22] Filed: Feb. 9, 1999

Related U.S. Application Data

[63] Continuation-in-part of application No. 09/119,470, Jul. 20, 1998, which is a continuation-in-part of application No. 09/009,487, Jan. 20, 1998.

[51] Int. Cl.[7] .................................................. A61B 19/00
[52] U.S. Cl. ......................... 604/408; 604/403; 215/247; 206/828
[58] Field of Search ..................................... 604/403, 408, 604/411–416; 215/247, 249; 206/828

[56] References Cited

U.S. PATENT DOCUMENTS

| | | |
|---|---|---|
| Re. 32,065 | 1/1986 | Ralston et al. . |
| 2,619,277 | 11/1952 | Shumann . |
| 4,088,166 | 5/1978 | Miller . |
| 4,150,744 | 4/1979 | Fennimore . |
| 4,509,197 | 4/1985 | Long . |
| 4,548,605 | 10/1985 | Iwamoto et al. . |
| 4,660,721 | 4/1987 | Mykleby . |
| 4,872,553 | 10/1989 | Suzuki et al. . |
| 4,892,537 | 1/1990 | Carmen et al. . |
| 4,976,707 | 12/1990 | Bodicky et al. . |
| 5,071,413 | 12/1991 | Utterberg . |
| 5,086,915 | 2/1992 | Yashima et al. . |
| 5,088,994 | 2/1992 | Porat . |
| 5,360,413 | 11/1994 | Leason et al. . |
| 5,391,150 | 2/1995 | Richmond . |
| 5,423,794 | 6/1995 | Adolf et al. . |
| 5,573,516 | 11/1996 | Tyner . |
| 5,728,087 | 3/1998 | Niedospial, Jr. . |

*Primary Examiner*—John G. Weiss
*Assistant Examiner*—Dennis Ruhl
*Attorney, Agent, or Firm*—Imre Balogh

[57] ABSTRACT

Multiple use universal connector designed for use in various containers having a fluid port for accessing to the content of the container or for transferring fluid into the container. The multiple use universal connector incorporates a diaphragm capable of being penetrated repeatedly by an access means such as a luer connector or a syringe having a sharp or blunt cannula for fluid communication between the content of the container and the access means. The multiple use universal connector re-seals itself after being penetrated and the access means removed therefrom.

20 Claims, 27 Drawing Sheets

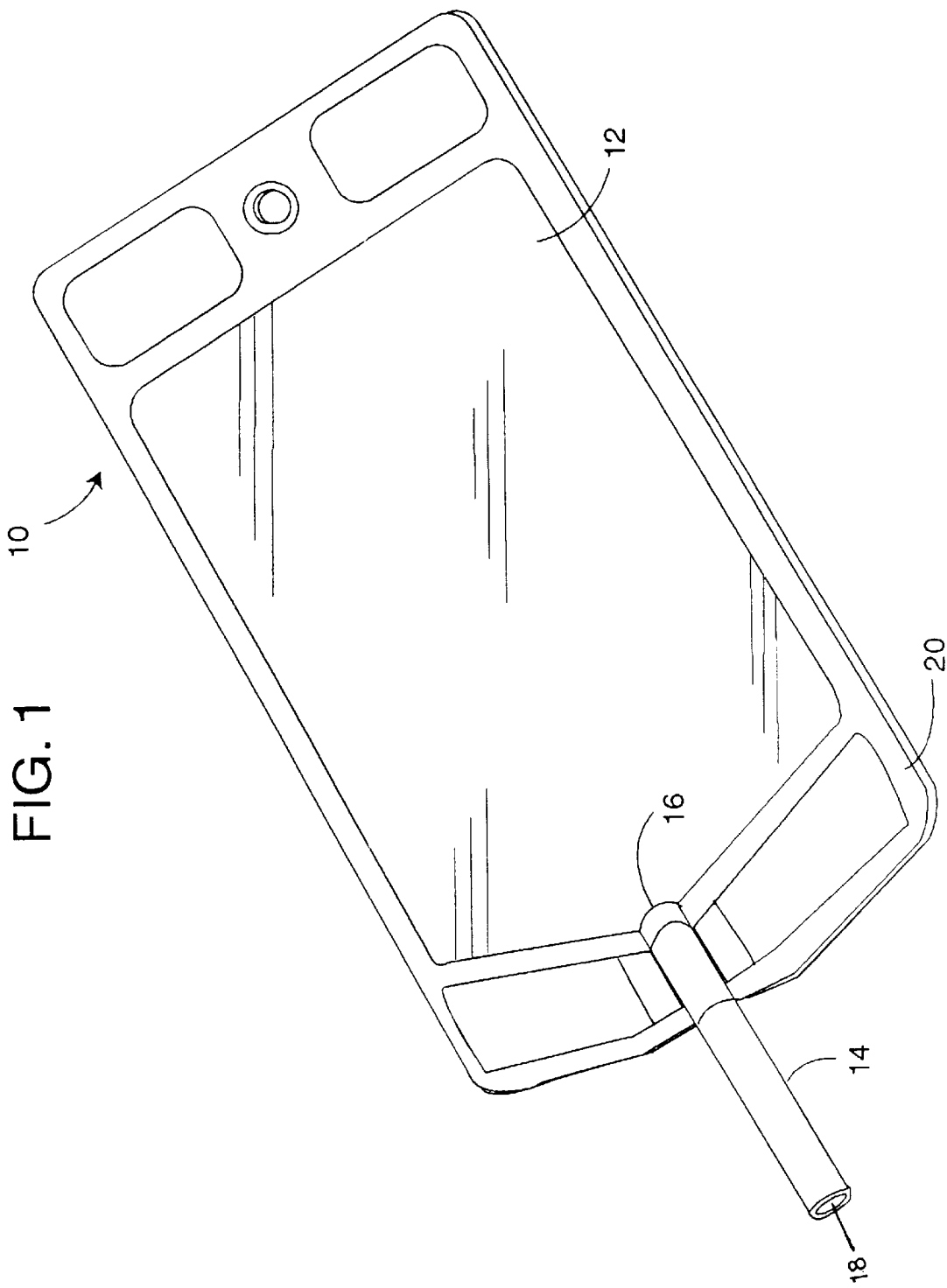

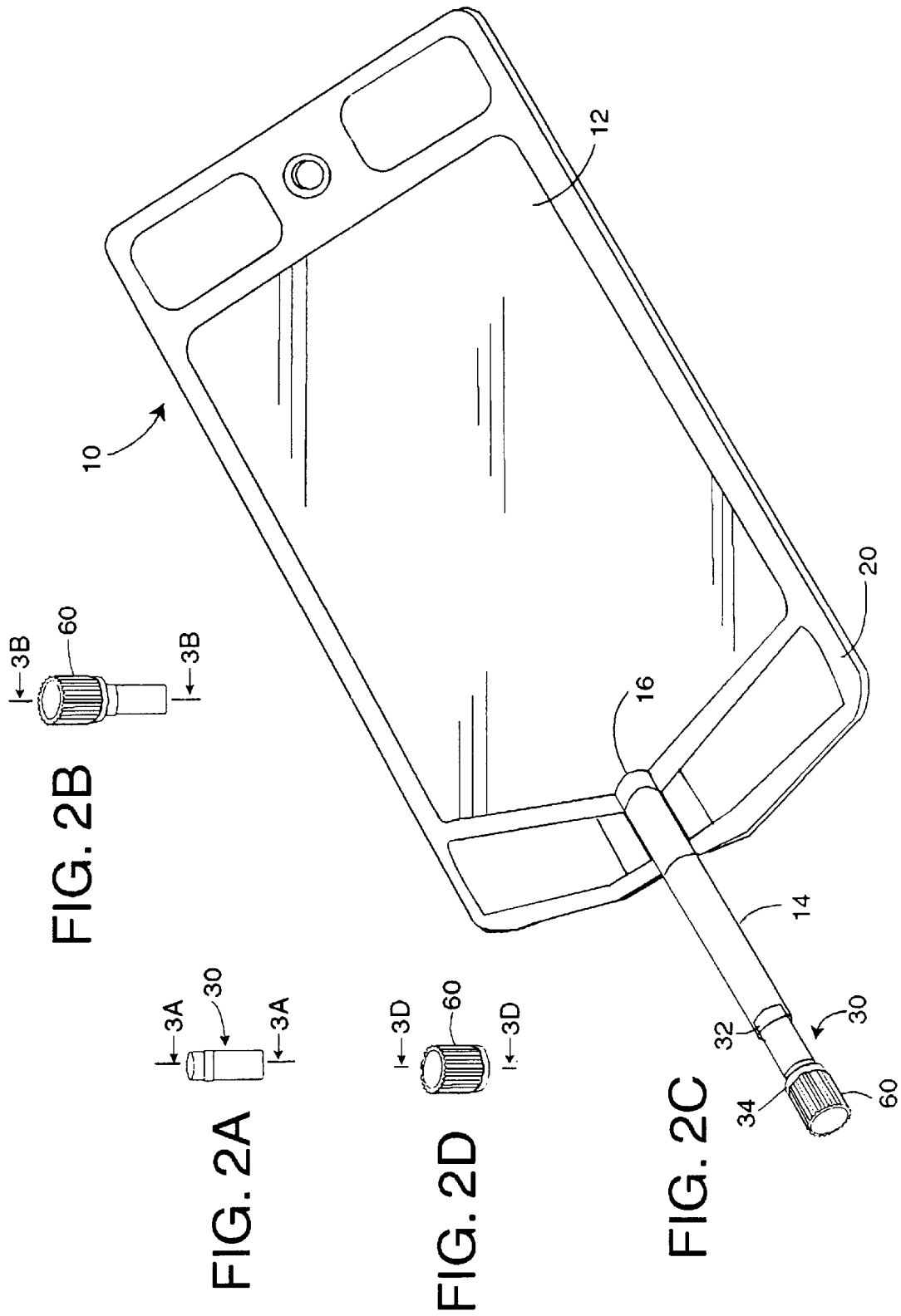

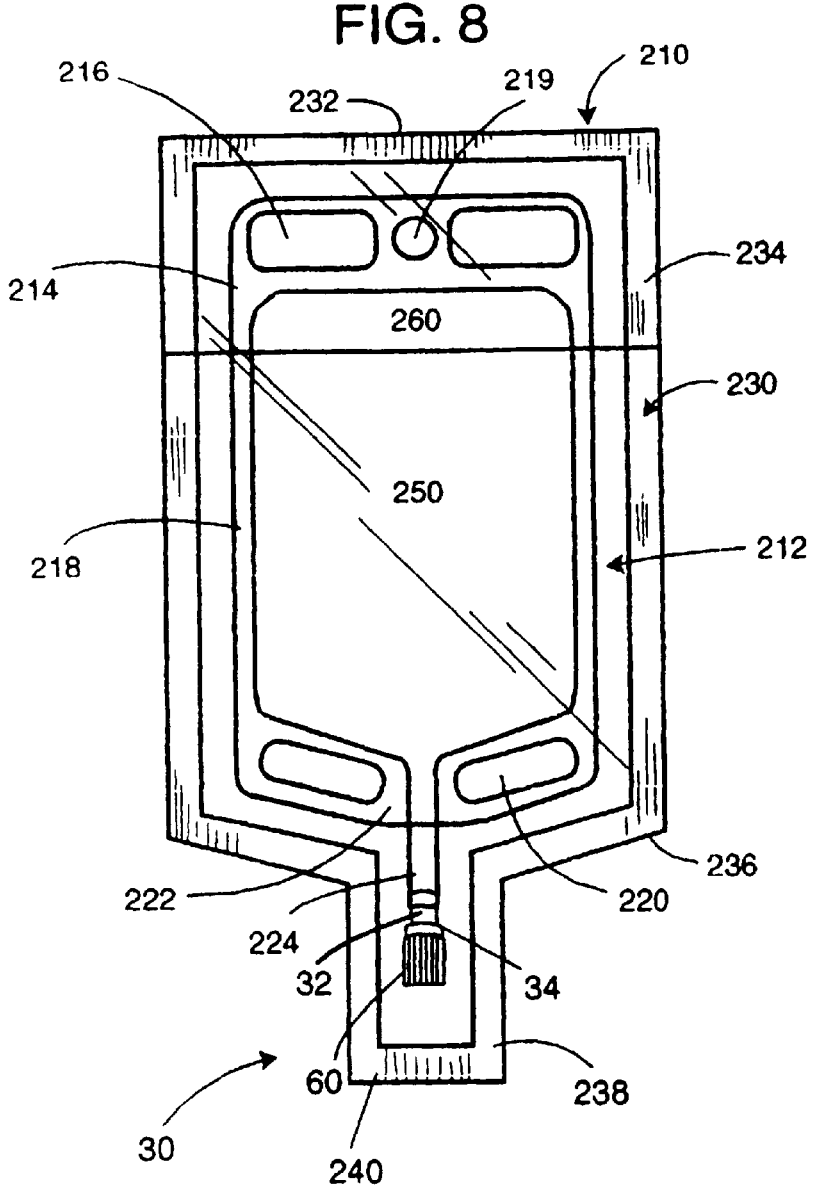
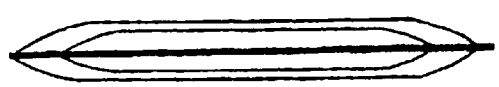

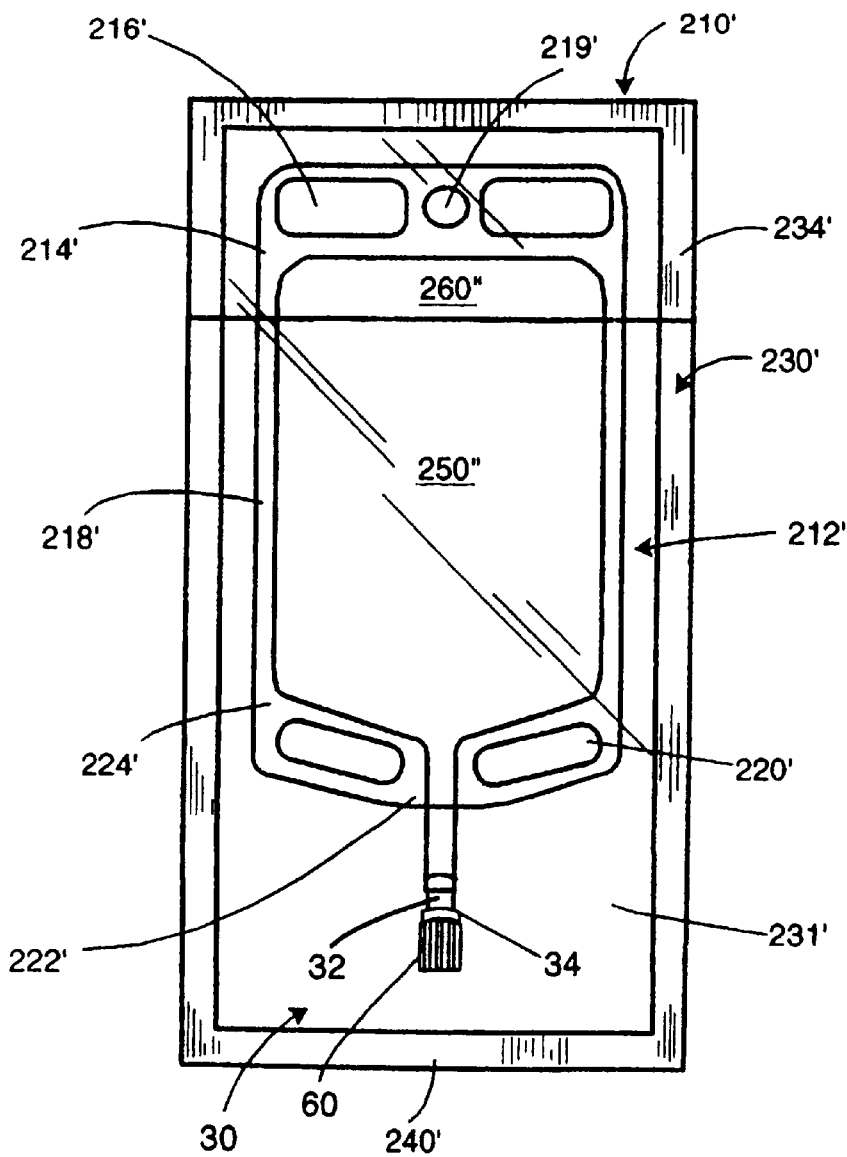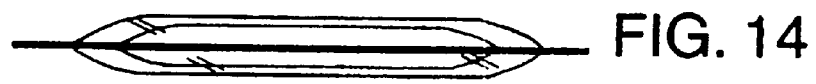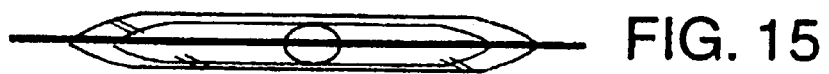

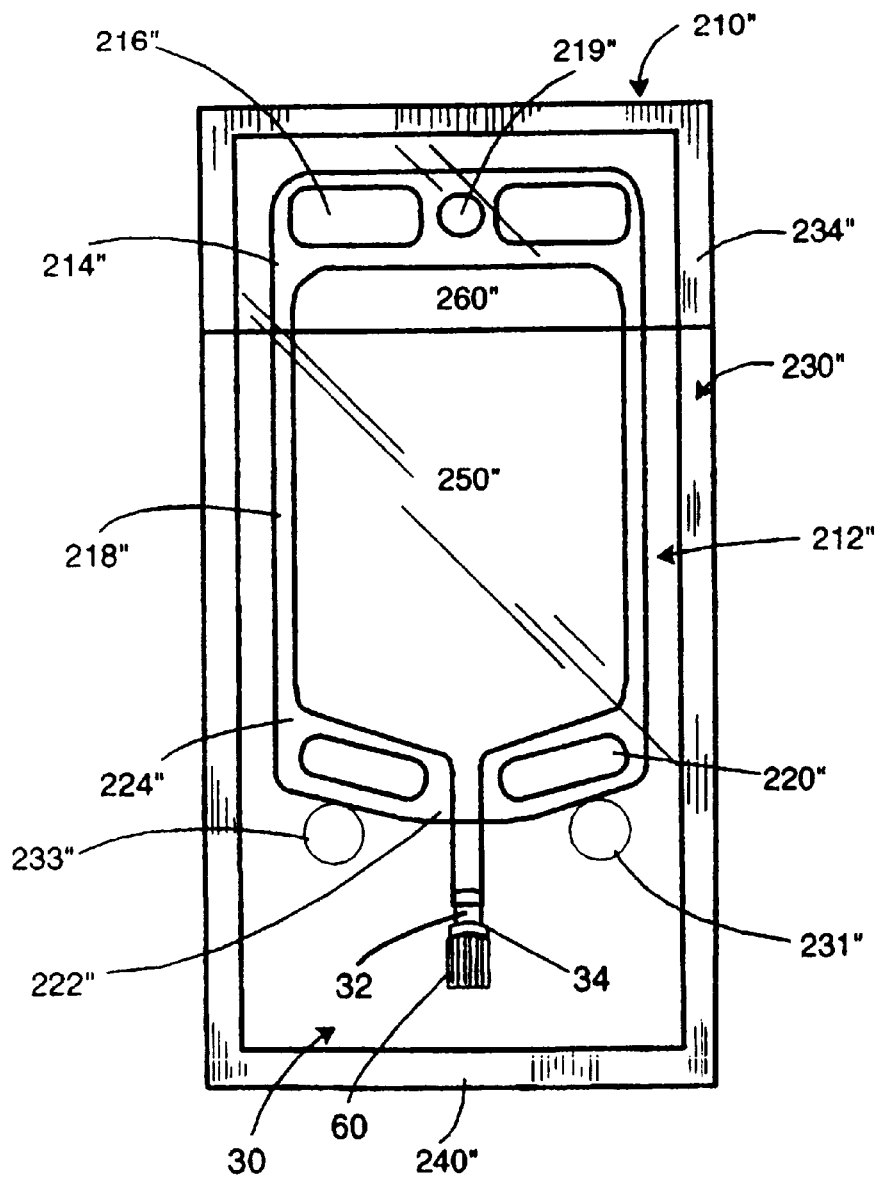
FIG. 16
FIG. 17
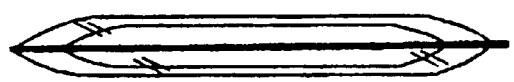
FIG. 18
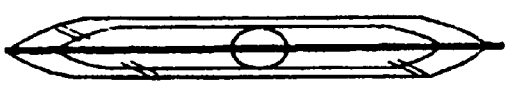
FIG. 19

MULTIPLE USE UNIVERSAL CONNECTOR

This application is a continuation-in-part of application Ser. No. 09/119,470, filed on Jul. 20, 1998, which in turn, is a continuation-in-part of application Ser. No. 09/009,487, filed on Jan. 20, 1998.

BACKGROUND OF THE INVENTION

1. Field of the Invention

This invention relates to a universal connector connectable to containers having fluid contents therein designed for delivery to a site of administration. More particularly, the invention relates to a universal connector having self-sealing means so that a pharmaceutical fluid contained in a container closed by the universal connector can be repeatedly accessed.

2. Reported Developments

Parenteral fluids, such as therapeutic drugs, diagnostic contrast media and nutrients are conventionally administered to a patient from a container, such as a collapsible bag or bottle having a fluid exit port. The fluid exit port may include means, such as a tube, spike or cannula, the distal end of which is in communication with the fluid content of the container and the proximal end of which is connected to the desired site on the patient. Conventionally, the proximal end of said means includes a needle that can puncture the skin of the patient. The fluid exit port is sealed by a membrane which is punctured by inserting a spike into the exit port when fluid delivery is desired.

One approach used by the prior art to penetrate the membrane covering the fluid exit port comprises the use of syringes or spikes which carry the danger of accidental injuries caused by the sharp points of the needles and spike. Such injuries accidentally inflicted on the health practitioner carry the further risk of getting infected with diseases such as AIDS. In order to reduce the danger of accidental injuries, spikes having relatively blunt tips were used. However, such spikes puncture a large area of the membrane and once the spikes are removed the membrane no longer seals the fluid exit port.

Another approach used by the prior art is the provision of a tubular member which is more blunt than a spike so that it is unlikely to penetrate the skin yet capable of penetrating the latex diaphragm type seals.

Still another approach used by the prior art is a valve positioned in the fluid exit port, the valve being operable by engagement with a spikeless or needleless IV component and contains a resilient valve disc positioned in the fluid passageway and blocks fluid flow when the disc is in the closed position, and allows fluid flow when the disc is in the open position.

Still another needleless connector of the prior art uses a resilient conical valve head in a housing. The conical valve head is positioned against the valve seat to form a seal. When the male fitting of a syringe, or some other device, is inserted into the inlet of the housing, it pushes the tip portion of the resilient valve head inwardly so that the valve head is deformed away from the valve seat thereby allowing fluid communication. In still other embodiments of the prior art, a needleless connector includes an elastomeric conical valve head biased against a conical valve seat by a helical spring to form a seal.

The above generally described devices have greatly reduced the risk of needle-stick associated injuries by use of syringes to withdraw medical fluids from collapsible bags and bottles.

However, there still exists the need to provide a universal connector which may be used with a wide variety of connection sites. A seal or diaphragm is a main component of the herein-described invention which does not require penetration by any sharp of even blunt object in order to establish fluid communication between the content of the container and the site of delivery. The seal or diaphragm serves as access means and provides for hermetic sealing, safe handling, sterilization and storing. The seal or diaphragm is designed for multiple use so that the medical fluid can be accessed repeatedly. After each withdrawal of the desired amount of the medical fluid, the seal or diaphragm self-seals itself thereby preventing contamination of the medical fluid by air-born particles such as dust and bacteria.

SUMMARY OF THE INVENTION

In accordance with the present invention there is provide a multiple use universal connector which can be used to repeatedly access the fluid content of a container or to repeatedly transfer a fluid into the container. The multiple use universal connector can be used in collapsible and non-collapsible bags, bottles and vials made of glass or polymeric material which contain a fluid exit port into which the universal connector is inserted sealing the fluid exit port. The fluid contained in the container may be a therapeutic liquid, diagnostic media or a nutritional formula which can be sterilized in bulk and then aseptically transferred into the container or it can be sterilized in the container stoppered with the universal connector. The multiple use universal connector is made of rigid or semi-rigid polymeric materials such as polyvinyl chloride, polyethylene and polypropylene.

The fluid in a container stoppered by the multiple use universal connector can be accessed by means well-known in the art, such as syringes having sharp or blunt needle cannulas. Preferably, the access means comprises a luer connector in order to prevent accidental injuries to health care workers and patients caused by the use of syringes.

The multiple use universal connector comprises:

(1) a connector body of tube-like configuration the distal end of which is designed to be slideably insertable into the fluid exit port, and the proximal end of which is designed to seal the content of the container by an elastomeric membrane and also to receive a removable cap; and (2) a removable cap threaded onto the proximal end of the connector which, prior to use, is removed so that the content of the container could be accessed by the use of a luer connector having a configuration that is similar to the configuration of the cap or by other access means, such as sharp or blunt needle cannulas.

The elastomeric membrane sealing the proximal end of the universal connector is of an inert, gas-impermeable polymeric material capable of flexing under internal or external pressures such as exerted thereon during steam sterilization. It preferably has a thickness of from about 0.001 mm to about 1.00 mm and a durometer of from about 25 to about 80 Shore A. It is capable of being ruptured by the twisting motion of a blunt luer connector or syringes having sharp or blunt needle cannula. The configuration of the elastomeric membrane is M-shaped having vertical leg portions and a top surface resembling a cup shape.

The tube-like body of the universal connector further comprises: first cap-locking ring on the proximal end of the body which serves as a male thread to receive the removable cap; and second cap-locking ring spaced from the first cap-locking ring towards the distal end of the tube-like body, which serves as stopping means for the cap when the cap is threaded onto the tube-like body of the universal connector.

Preferred medical containers used in combination with the multiple use universal connector are those disclosed in copending applications (1) Serial Number 09/027,325, (2) Serial Number 08/900,739 and (3) Serial Number 09/196,084 each of which is incorporated by reference herein in its entirety constituting first, second and third embodiments of the present invention.

First Embodiment (1) In the first embodiment, a flexible, collapsible medical container equipped with the multiple use universal connector is packaged in an overwrap in order to prevent degradation of a light-sensitive medical fluid contained in the medical container.

The medical container in combination with the multiple use universal connector comprising:

first and second transparent polymeric sheets having a square, round, oval, hexagonal, octagonal or rectangular configuration superimposed and sealed together at their periphery defining an interior reservoir, said container having a top portion and a bottom portion;

an access port located at the bottom center portion sealed between said first and second polymeric sheets removably covered with a cap, said access port is designed for allowing filling of the medical container with the medical fluid and access thereto by an access means for delivery of the medical fluid to a patient, said access means comprising the multiple use universal connector.

The overwrap comprises:

first and second polymeric sheets having a square, round, oval hexagonal, octagonal or rectangular configuration superimposed and sealed together at their periphery hermetically sealing said medical container, wherein a substantial portion of said first and said second polymeric sheet is opaque preventing penetration of UV rays into the content of said medical container and wherein the remaining minor portion of said first and said second polymeric sheet is transparent allowing partial viewing of the medical container and its content, or first and second transparent UV rays barrier polymeric sheets having a square, round, oval, hexagonal, octagonal or rectangular configuration superimposed and sealed together at their periphery hermetically sealing said medical container preventing penetration of UV rays into the content of said medical container and allowing viewing of the medical container and its content.

Second Embodiment

In the second embodiment of the present invention a flexible unitary plastic container having a reinforcing means therein is equipped with the multiple use universal connector comprising:

a) first and second flexible plastic sheets having a generally rectangular configuration superimposed and sealed together at their periphery to form a pouch defining an interior, said pouch having a top and a bottom portion; said bottom portion terminates in a first angle and a second angle of from about 5° to about 45°, preferably of from about 10° to about 30°, and most preferably from 10° to 20° from the center of said bottom portion to direct and facilitate the flow of the solution contained in the pouch towards an access port;

b) an access member integral with said pouch located at the center of the bottom portion of said pouch for allowing filling of the container with a parenteral solution and access thereto for its delivery, said access member comprising:

1) an access port located below the bottom portion of said pouch where said first angle and said second angle meet;

2) a flexible tubing one end of which is integral with said access port and the other end of which is equipped with the multiple use universal connector; and c) an oval shaped reinforcing means containing ribs therein positioned horizontally in the pouch, preferably at the center thereof.

Third Embodiment

In a third embodiment of the present invention a flexible, unitary container of square, round, oval, rectangular, hexagonal or octagonal configuration is equipped with the multiple use universal connector comprising:

a) first and second non-coplanar polymeric sheets superimposed and sealed together at their periphery to form a pouch defining an interior, wherein said first and second non-coplanar polymeric sheets form a concavo-convex shape three dimensional reservoir prior to being filled with a fluid and subsequent thereto; and b) at least one access member integral with said pouch located at the center of the bottom portion of said pouch for allowing filling of the pouch with a fluid and access thereto for its delivery, said access member comprising:

at least one access port located at the bottom portion of said pouch, said access port is equipped with the multiple use universal connector.

BRIEF DESCRIPTION OF THE DRAWINGS

FIGS. 1 to 7D show the multiple use universal connector in conjunction with a generalized rectangular medical bag designated in FIG. 1. In these drawings, like numerals indicate like elements and primes (') indicate counterparts of like elements.

Figure 3A:
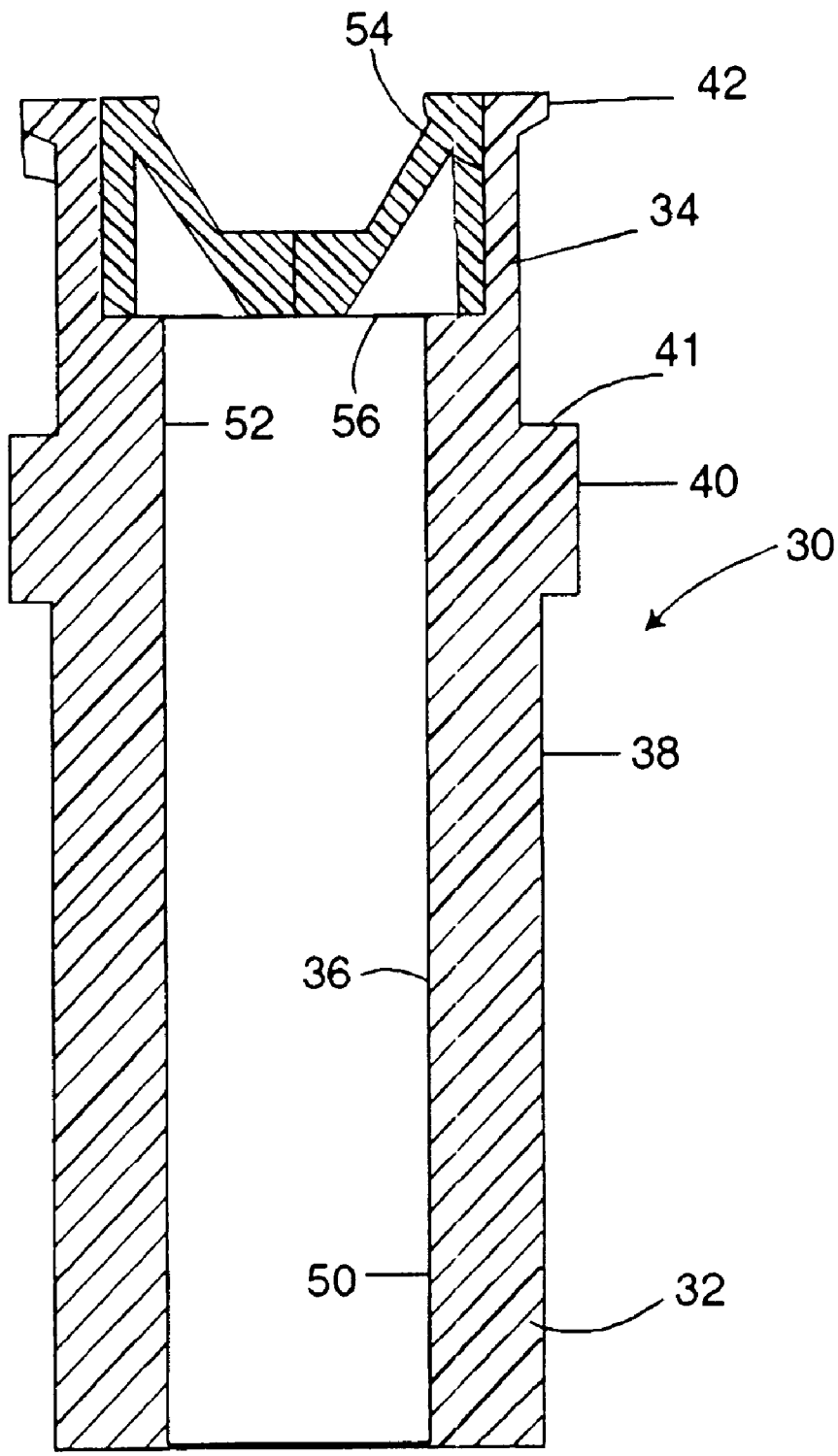
Figure 3B:
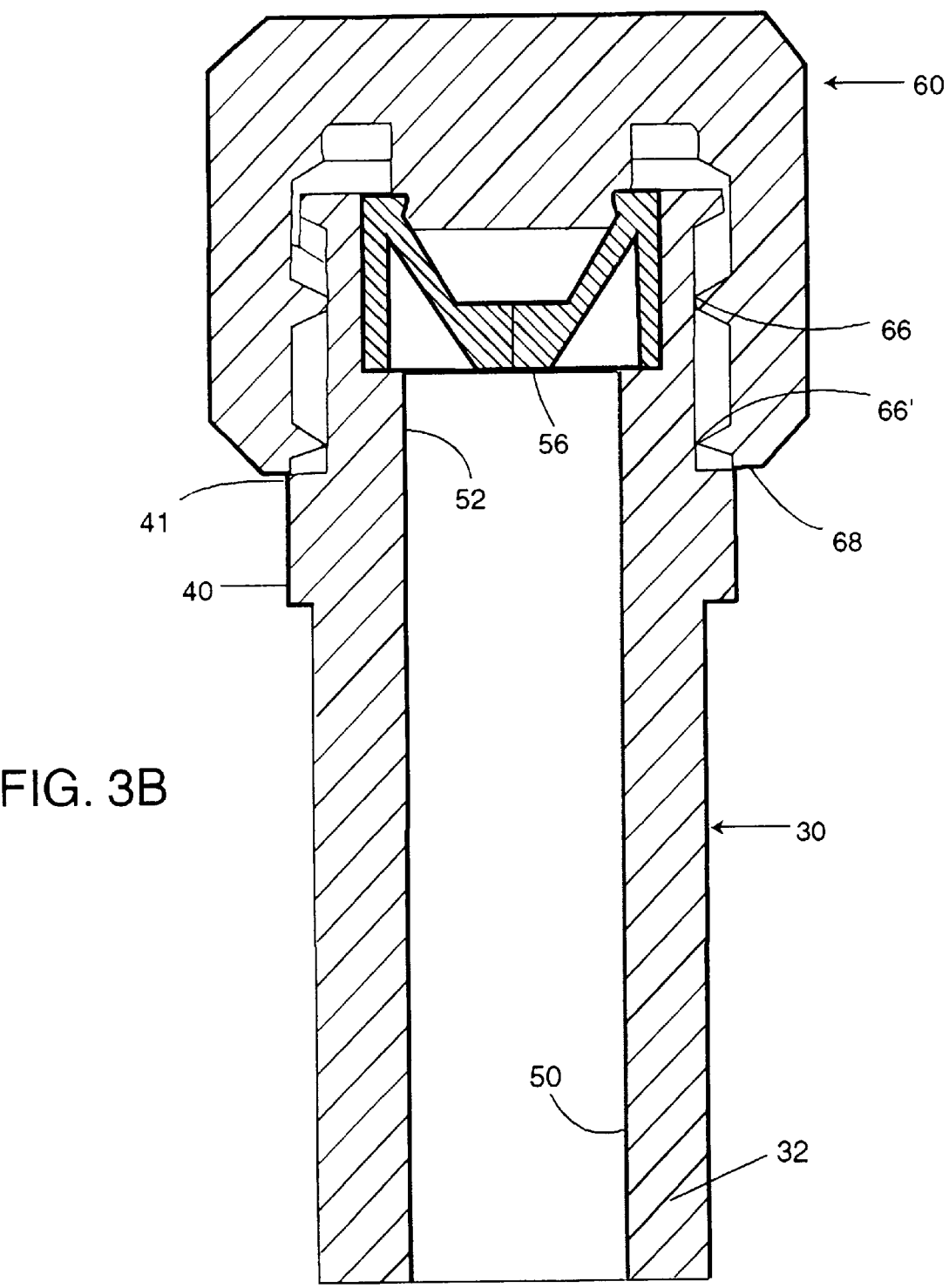
Figure 3C:
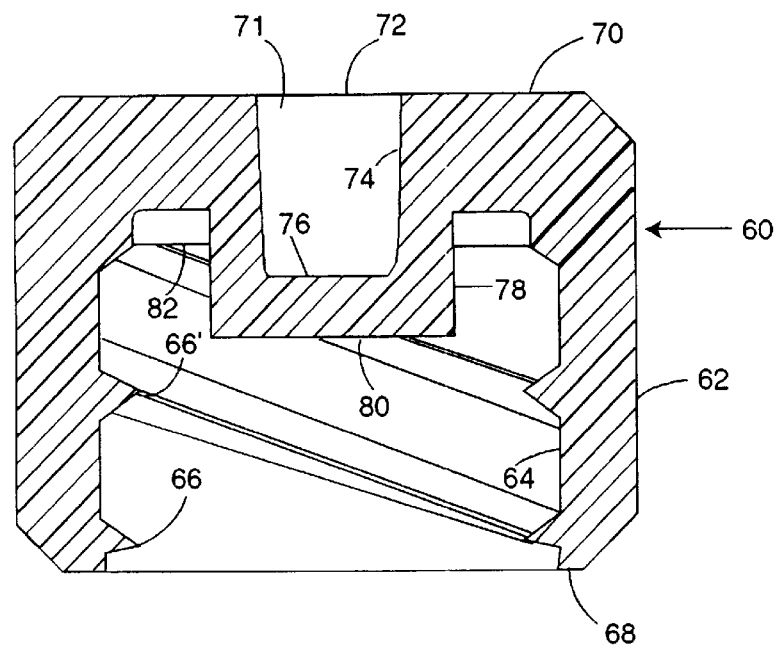
Figure 3D:
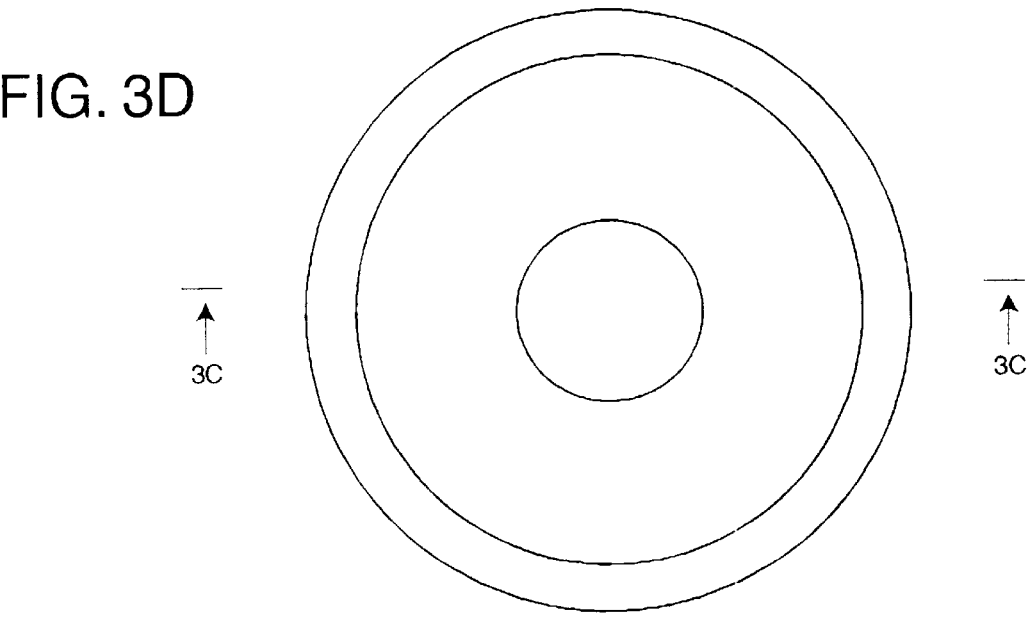
Figure 4A:
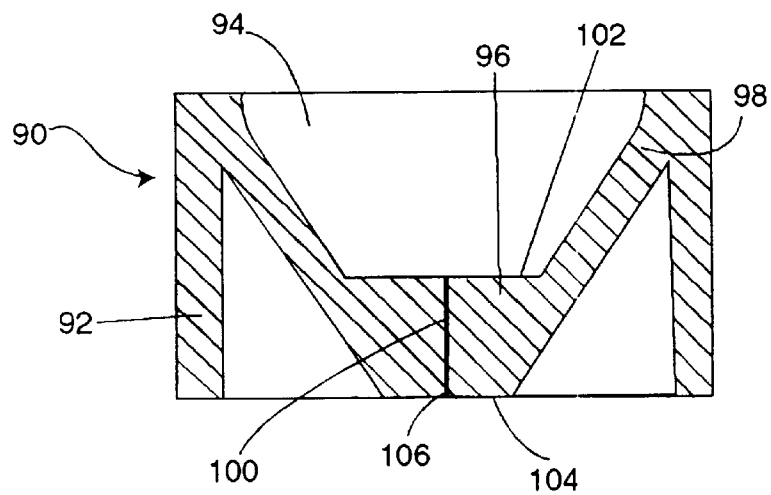
Figure 4B:
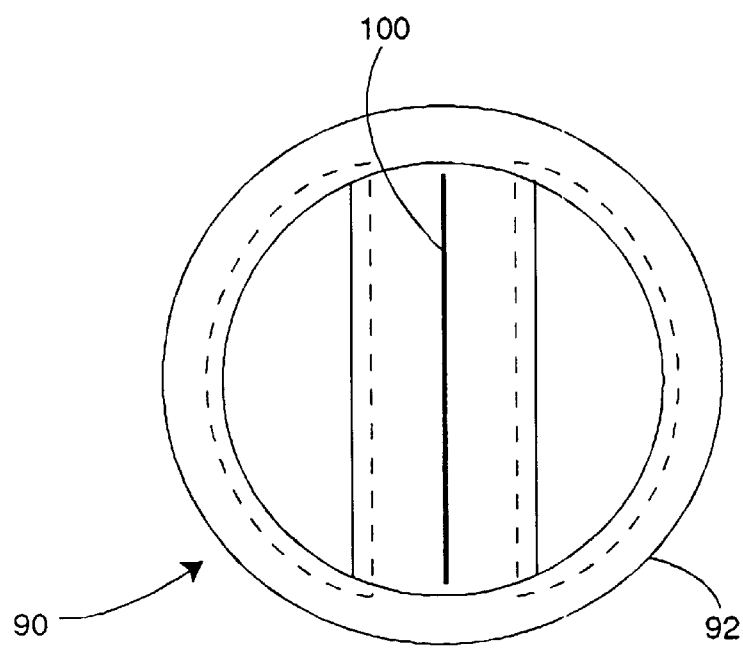
Figure 5A:
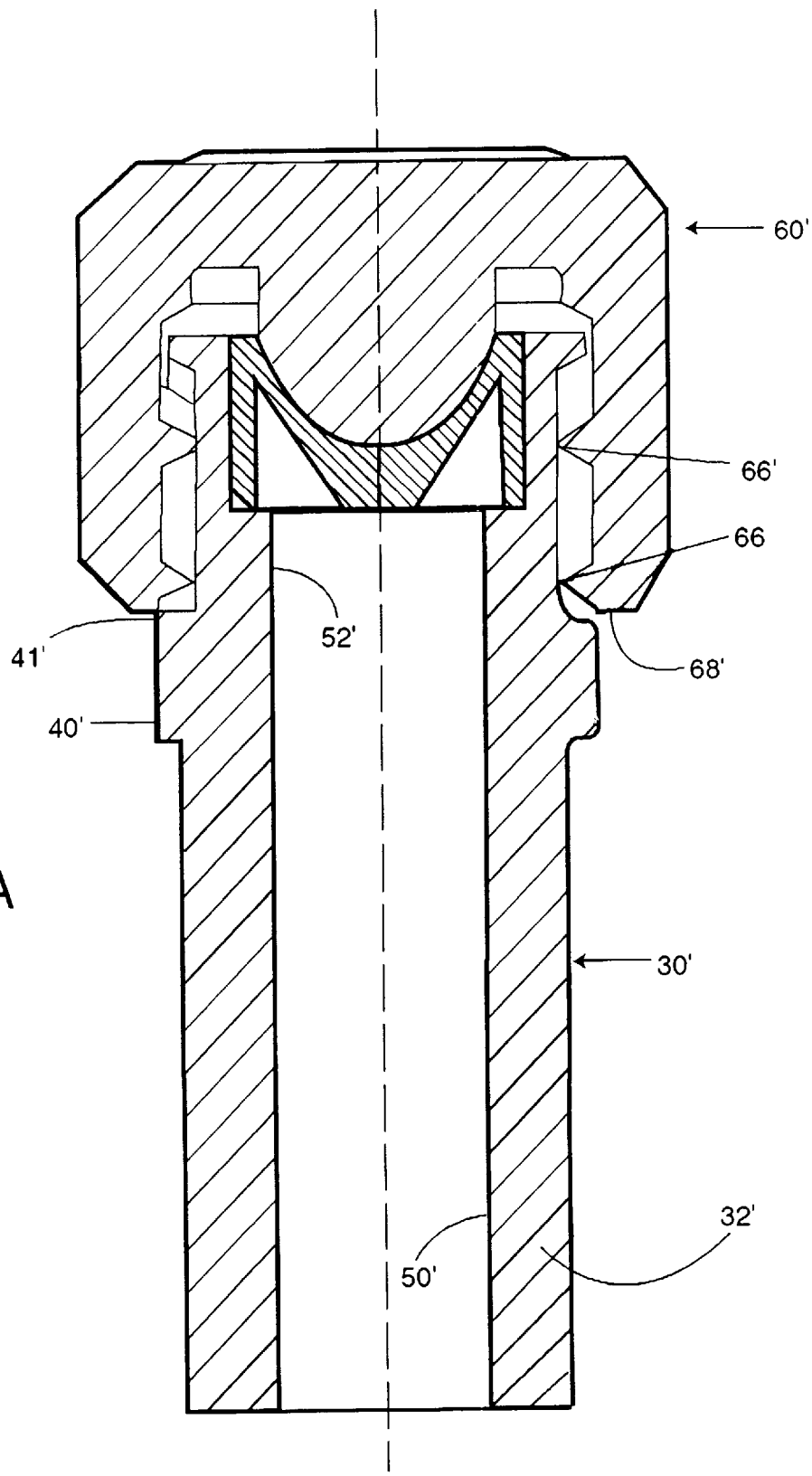
Figure 5B:
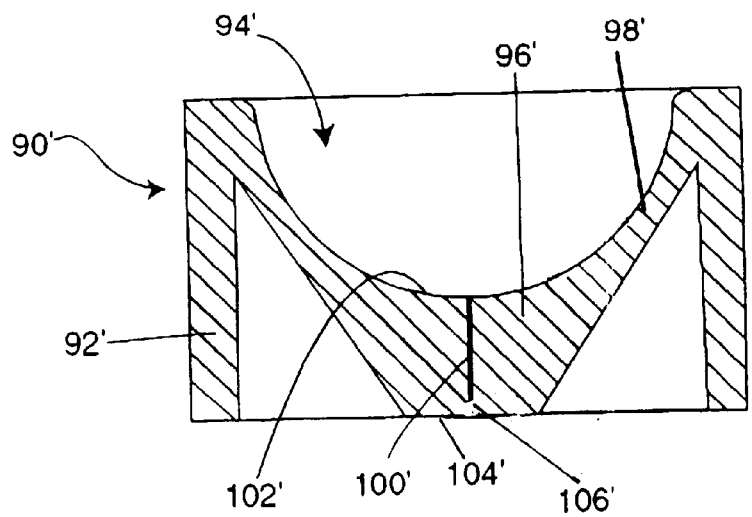
Figure 5C:
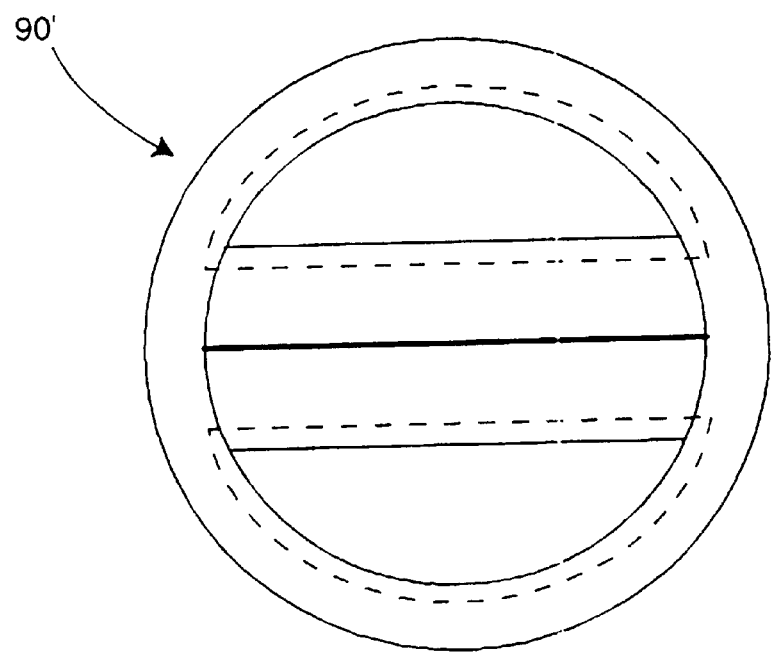
Figure 6:
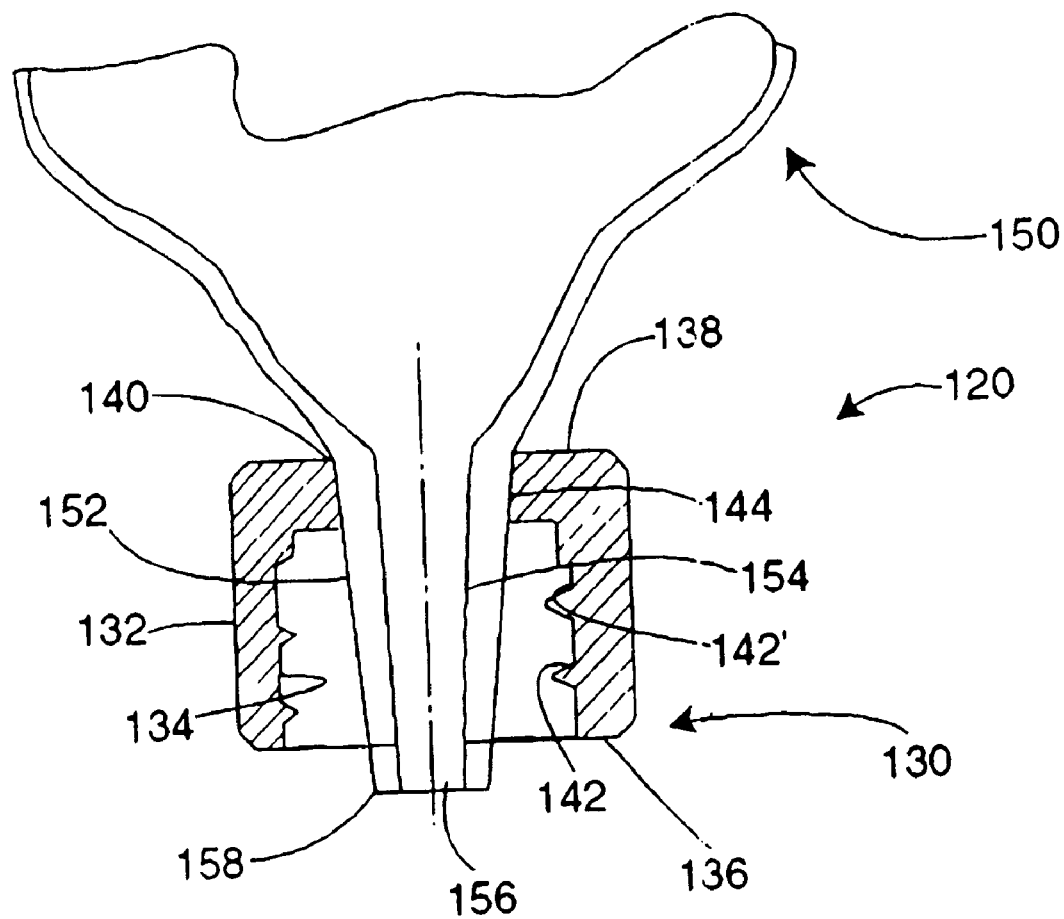
Figure 7A:
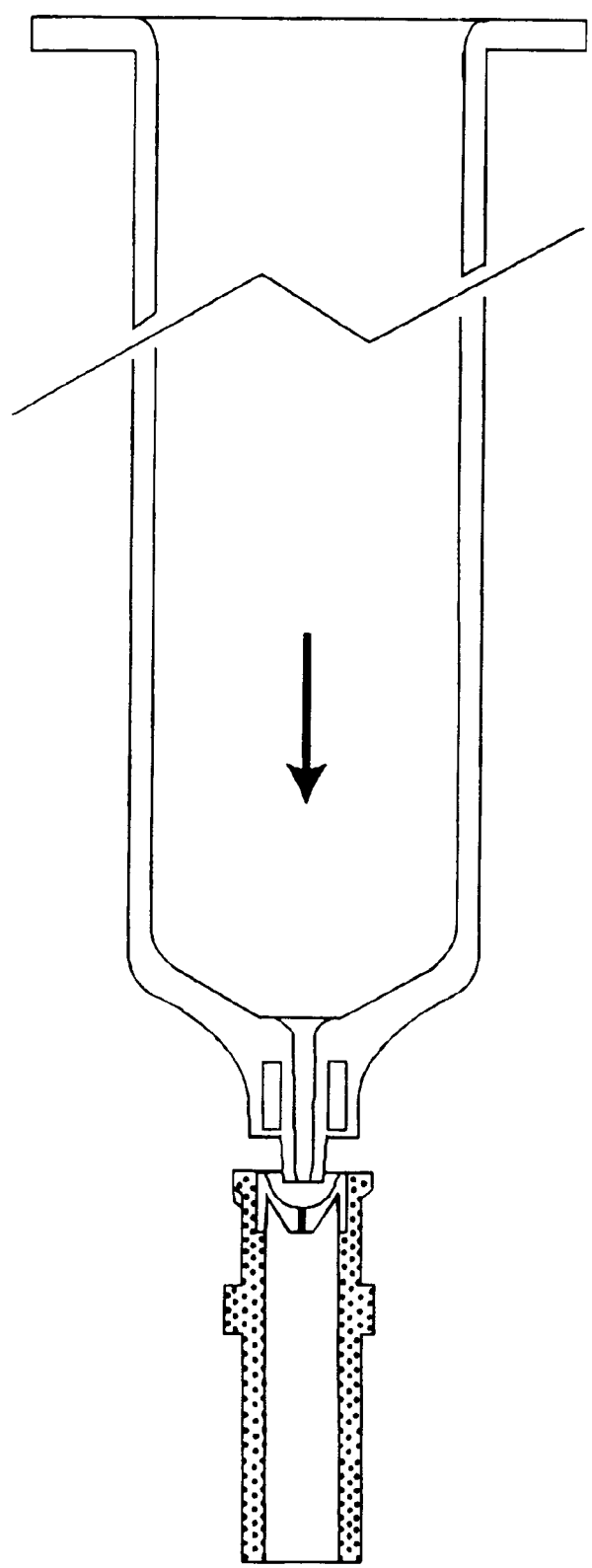
Figure 7B:
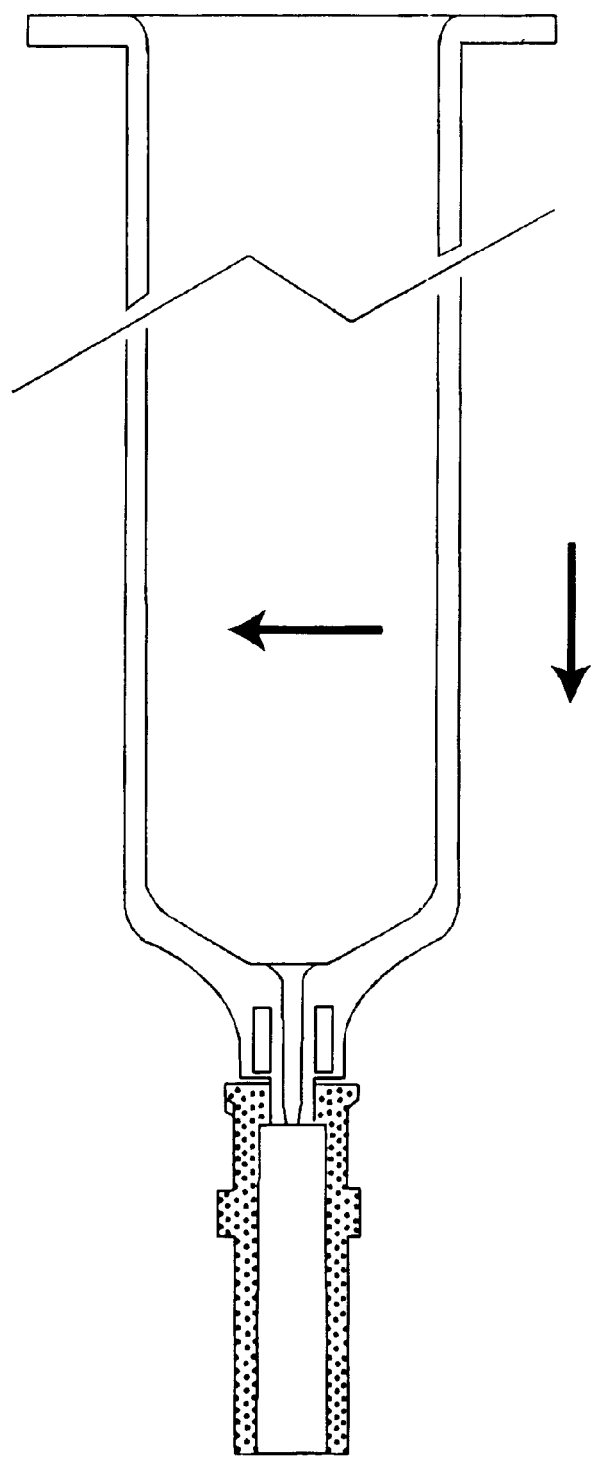
Figure 7C:
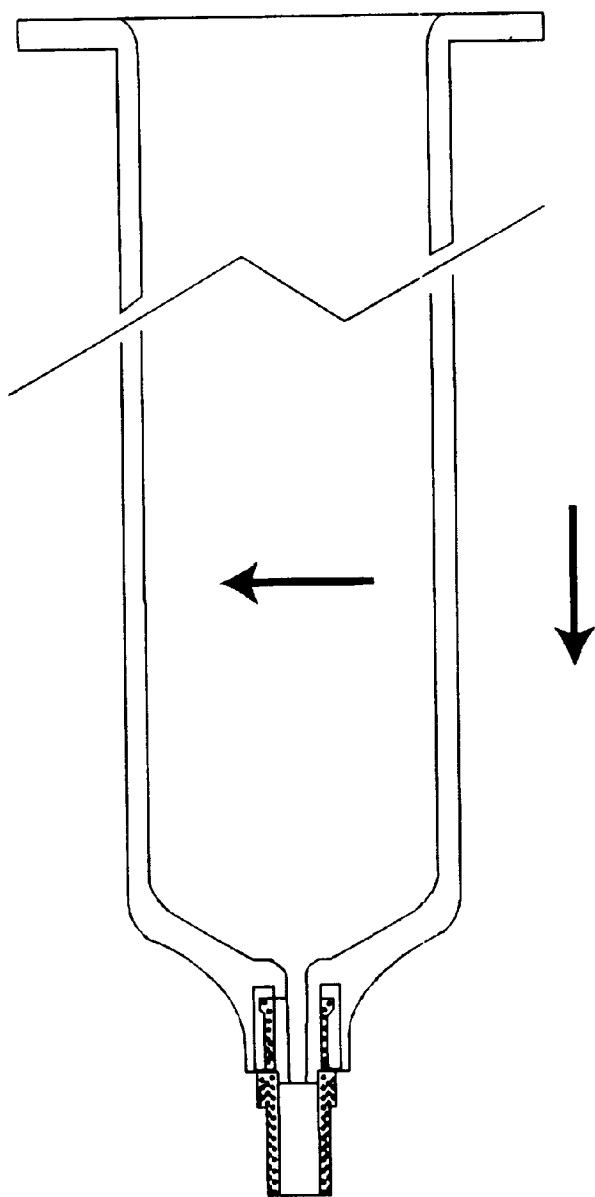
Figure 7D:
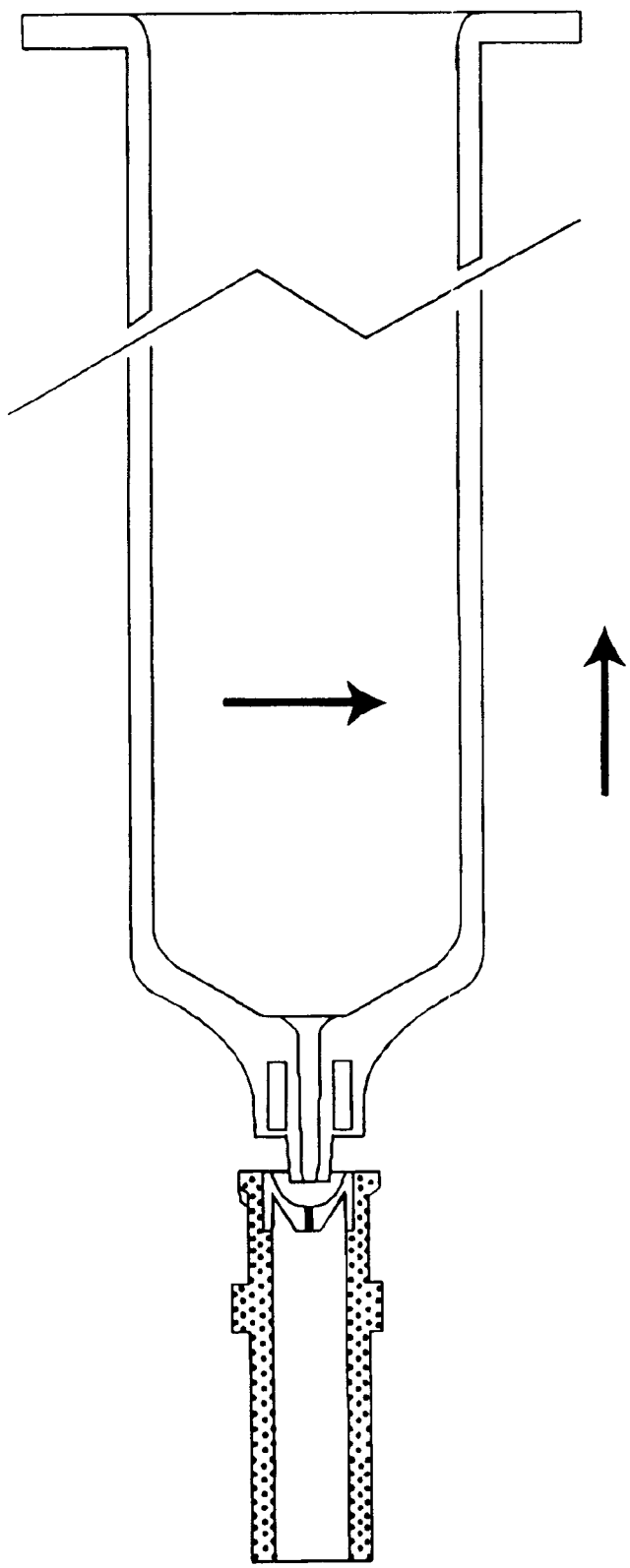

Accordingly:

FIG. 1 is a perspective view of a medical bag;

FIG. 2A is a perspective view of the multiple use universal connector of the present invention without the cap attached;

FIG. 2B is a perspective view of the multiple use universal connector of the present invention with the cap attached;

FIG. 2C is a perspective view of the multiple use universal connector of the present invention with the cap attached and connected to the medical bag of FIG. 1;

FIG. 2D is a perspective view of the cap;

FIG. 3A is a cross-section of the multiple use universal connector without the cap attached taken along the line 3A—3A of FIG. 2A;

FIG. 3B is a cross-section of the multiple use universal connector with the cap attached taken along the line 3B—3B of FIG. 2B;

FIG. 3C is a cross-section of the cap taken along the line 3D—3D of FIG. 2D;

FIG. 3D is a top plan view of the cap shown in FIG. 2D;

FIG. 4A is a greatly enlarged cross-section of the M-shaped diaphragm shown in FIG. 3A;

FIG. 4B is a top plan view of the M-shaped diaphragm shown in FIG. 4A;

FIG. 5A is a cross-sectional view of another embodiment of the multiple use universal connector with the cap attached, wherein the M-shaped diaphragm has a smooth, semi-circular top surface;

FIG. 5B is a greatly enlarged cross-section of the M-shaped diaphragm shown in FIG. 5A;

FIG. 5C is a top plan view of the M-shaped diaphragm shown in FIG. 5B;

FIG. 6 is a cross-section of a luer connector attached to the multiple use universal connector of the present invention;

FIG. 7A is a cross-section of the multiple use universal connector prior to penetration of the diaphragm by the luer connector of a syringe;

FIG. 7B is a cross-section of the multiple use universal connector at initial penetration and break-through of the diaphragm by the luer connector of a syringe;

FIG. 7C is a cross-section of the multiple use universal connector at complete penetration of the diaphragm by a luer connector whereby full flow access of the content of the container is achieved; and FIG. 7D is a cross-section of the multiple use universal connector after removal of a luer connector whereby the diaphragm reseals itself.

FIGS. 8 to 19 show the multiple use universal connector in conjunction with the first embodiment of the present invention comprising a flexible, collapsible medical container equipped with the multiple use universal connector packaged in an overwrap.

Accordingly:

FIG. 8 is a plan view of a medical container and its overwrap package having a bottle shape in accordance with the present invention;

FIG. 9 is a side elevational view of the medical container and its overwrap package shown in FIG. 8;

FIG. 10 is a top plan view of the medical container and its overwrap package shown in FIG. 8;

FIG. 11 is a bottom plan view of the medical container and its overwrap package shown in FIG. 8;

FIG. 12 is a plan view of another embodiment of the present invention showing a medical container and its overwrap package having a rectangular configuration;

FIG. 13 is a side plan view of the medical container and its overwrap package shown in FIG. 12;

FIG. 14 is a top plan view of the medical container and its rectangular overwrap package shown in FIG. 12;

FIG. 15 is a bottom plan view of the medical container with its overwrap package shown in FIG. 12;

FIG. 16 is a plan view of another embodiment of the present invention showing a medical container and its rectangular overwrap package wherein the medical container is sealed to its overwrap package at least at two point spaced from each other which are to prevent sliding movement of the medical container within its overwrap;

FIG. 17 is a side plan view of the medical container and its overwrap package shown in FIG. 16;

FIG. 18 is a top plan view of the medical container and its overwrap package shown in FIG. 16; and FIG. 19 is a bottom plan view of the medical container and its overwrap package shown in FIG. 16.

Figure 20:
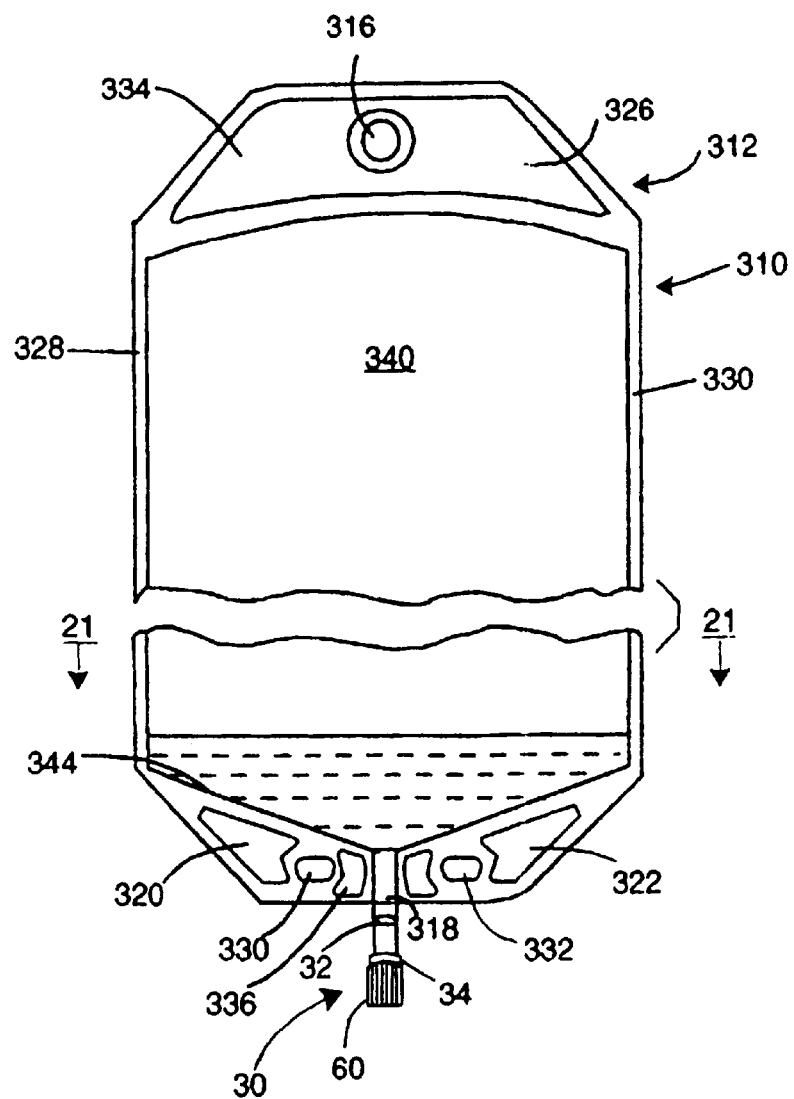
Figure 21:
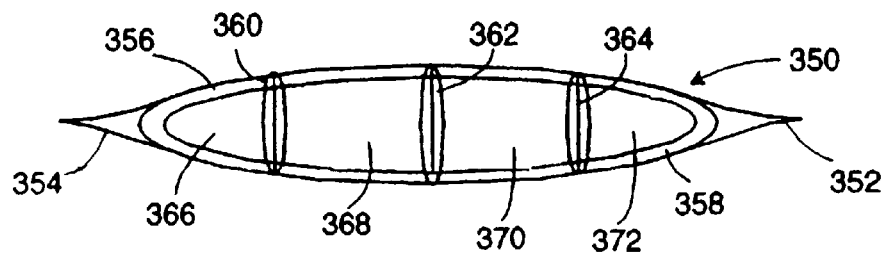

FIGS. 20 and 21 show the multiple use universal connector in conjunction with the second embodiment of the present invention comprising a flexible plastic container equipped with the multiple use universal connector.

FIG. 20 is a plan view of the flexible container showing an access member or port and the multiple use universal connector in the access member or port; and FIG. 21 is a cross-section showing a reinforcing means, containing ribs therein, taken along the line 21—21 of FIG. 20.

FIGS. 22–31 show the multiple use universal connector in conjunction with the third embodiment of the present invention comprising a flexible, unitary container equipped with the multiple use universal connector.

Figure 22:
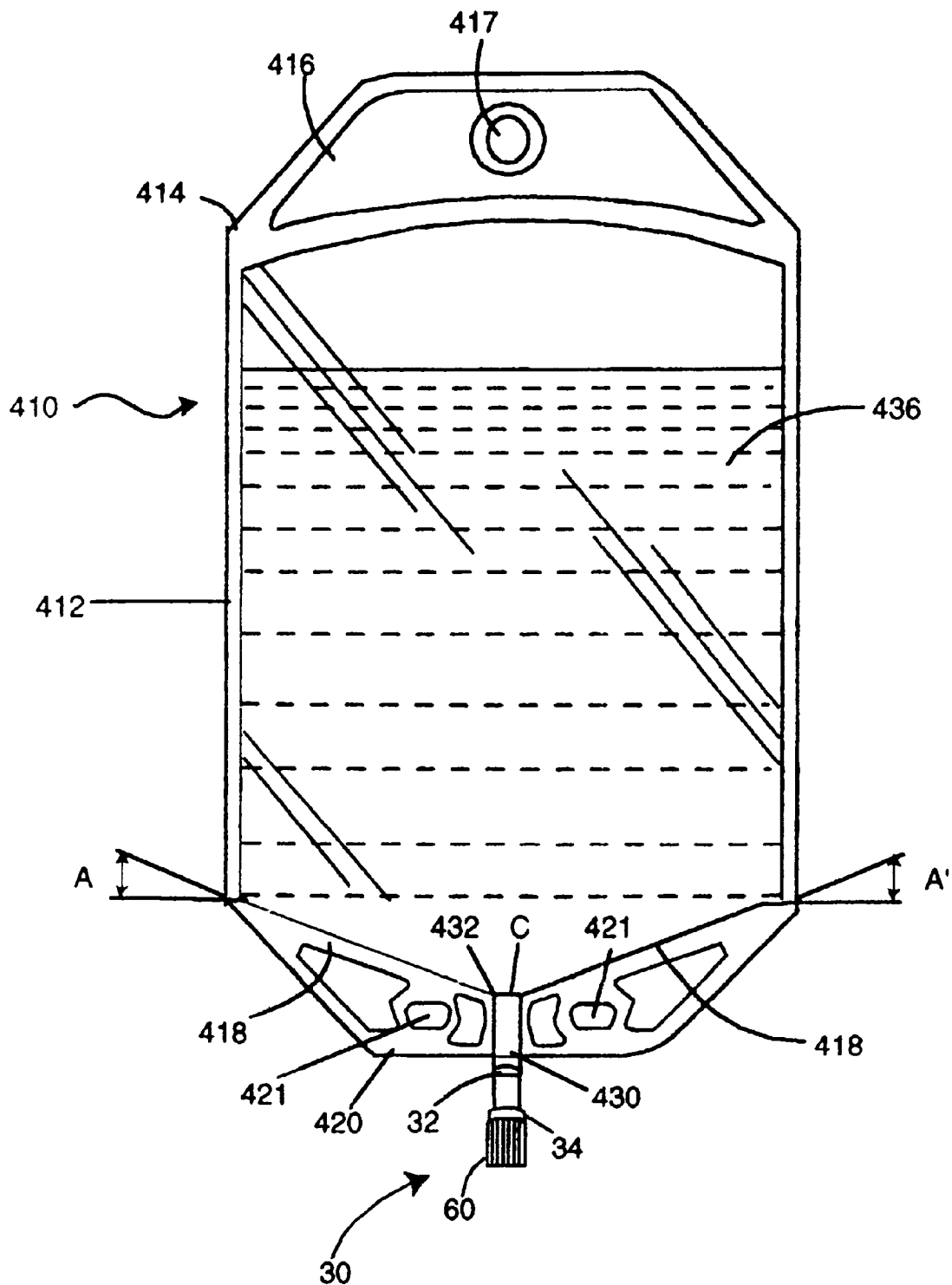
Figure 23:
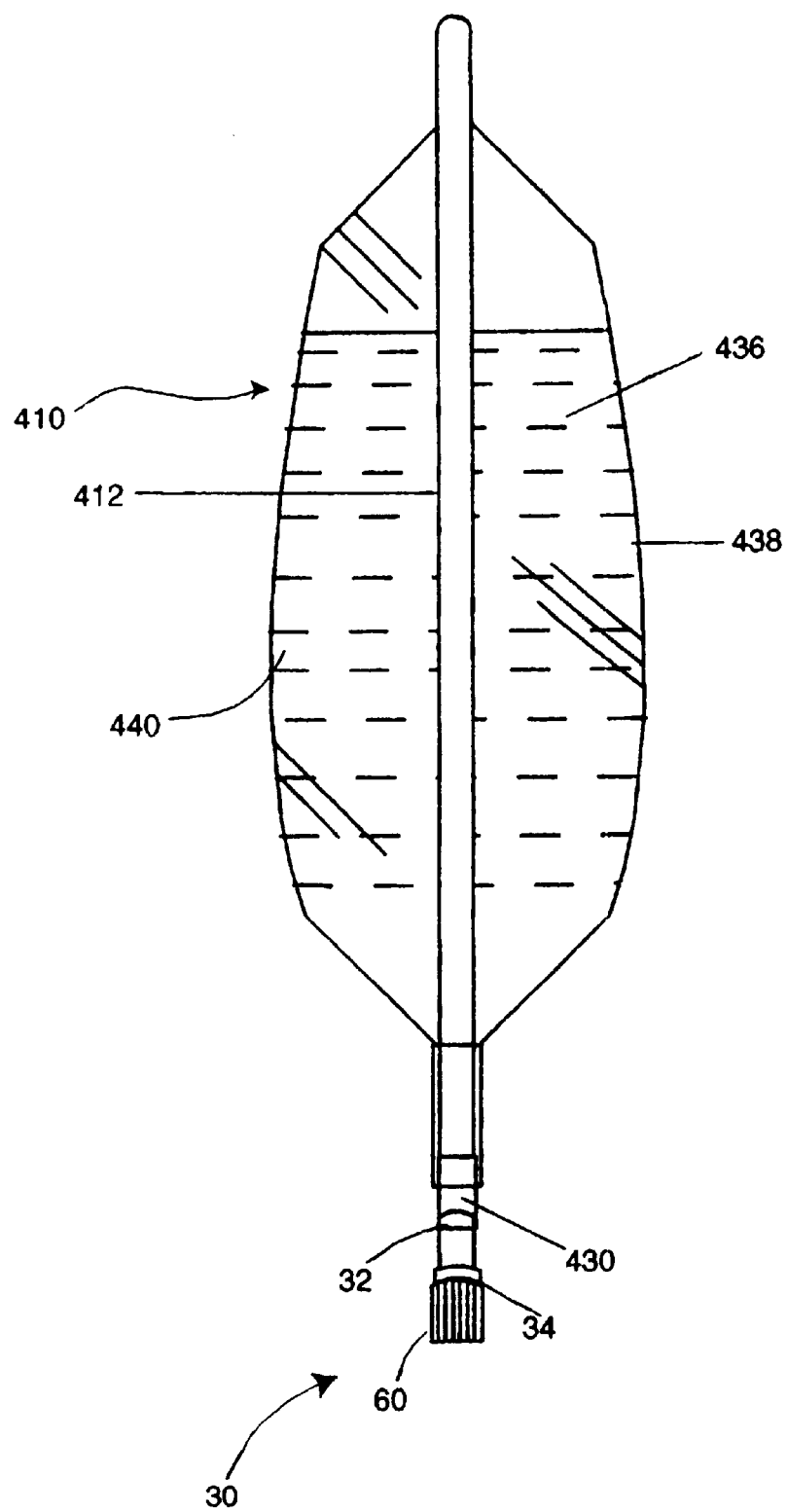
Figure 24:
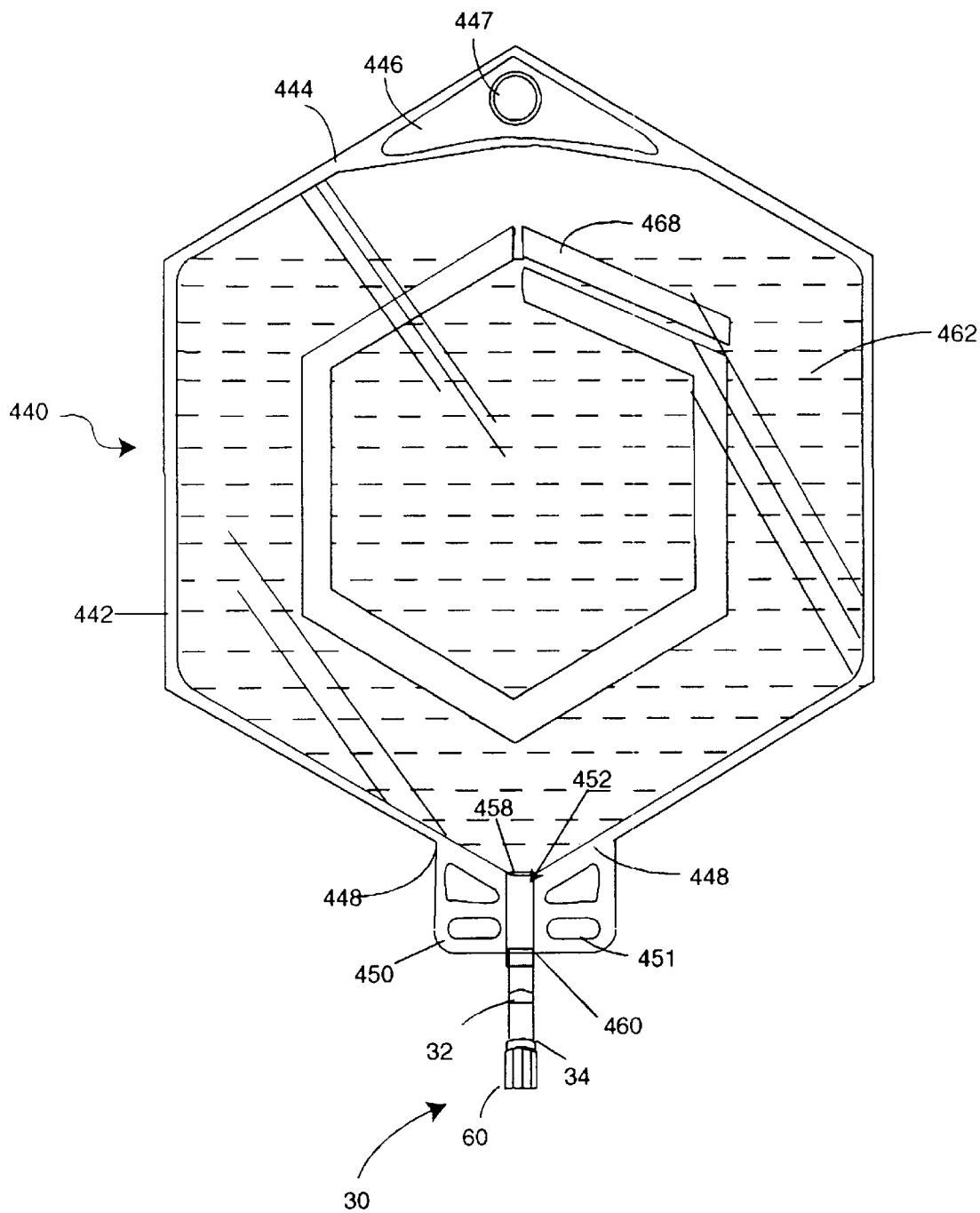
Figure 25:
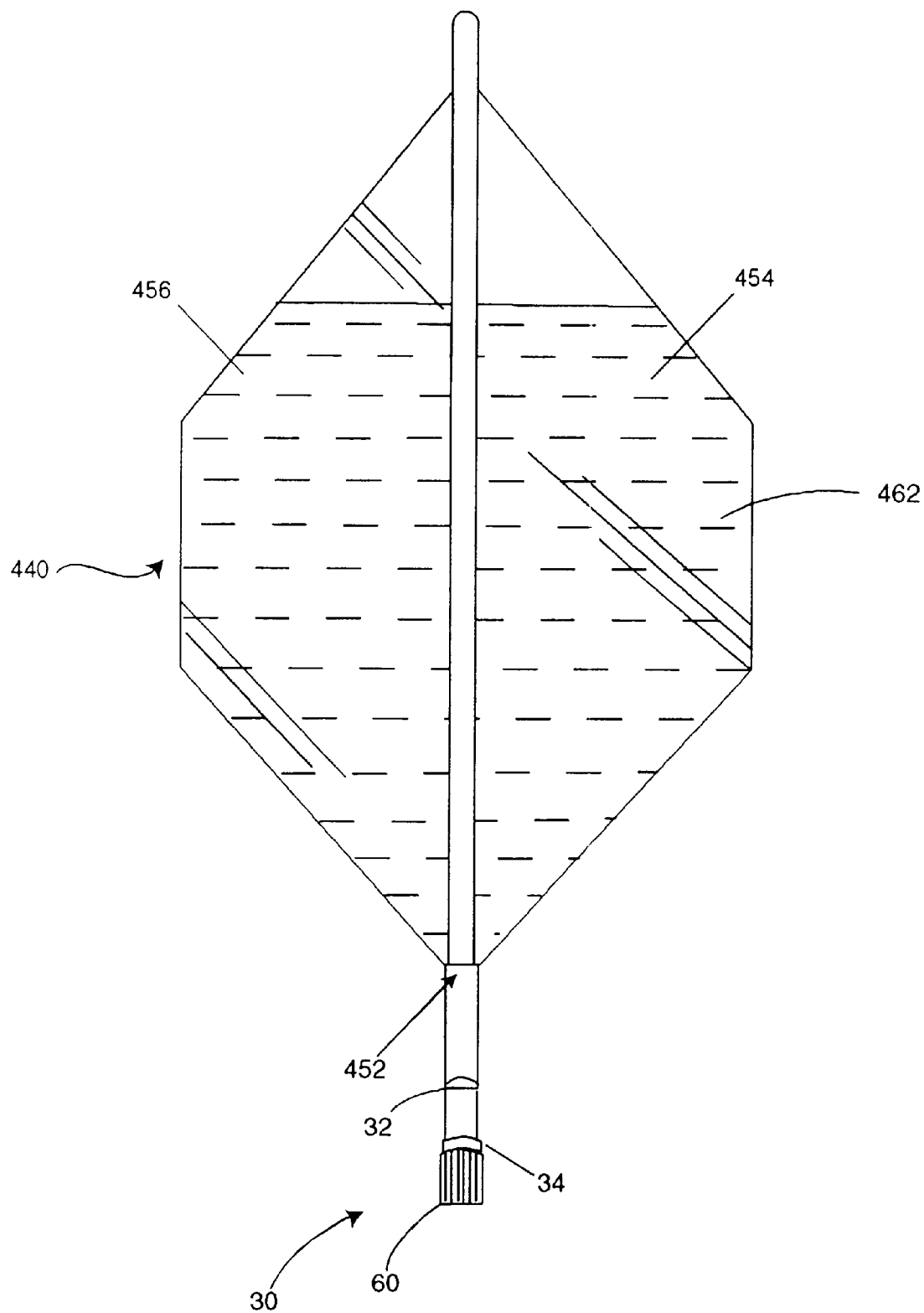
Figure 26:
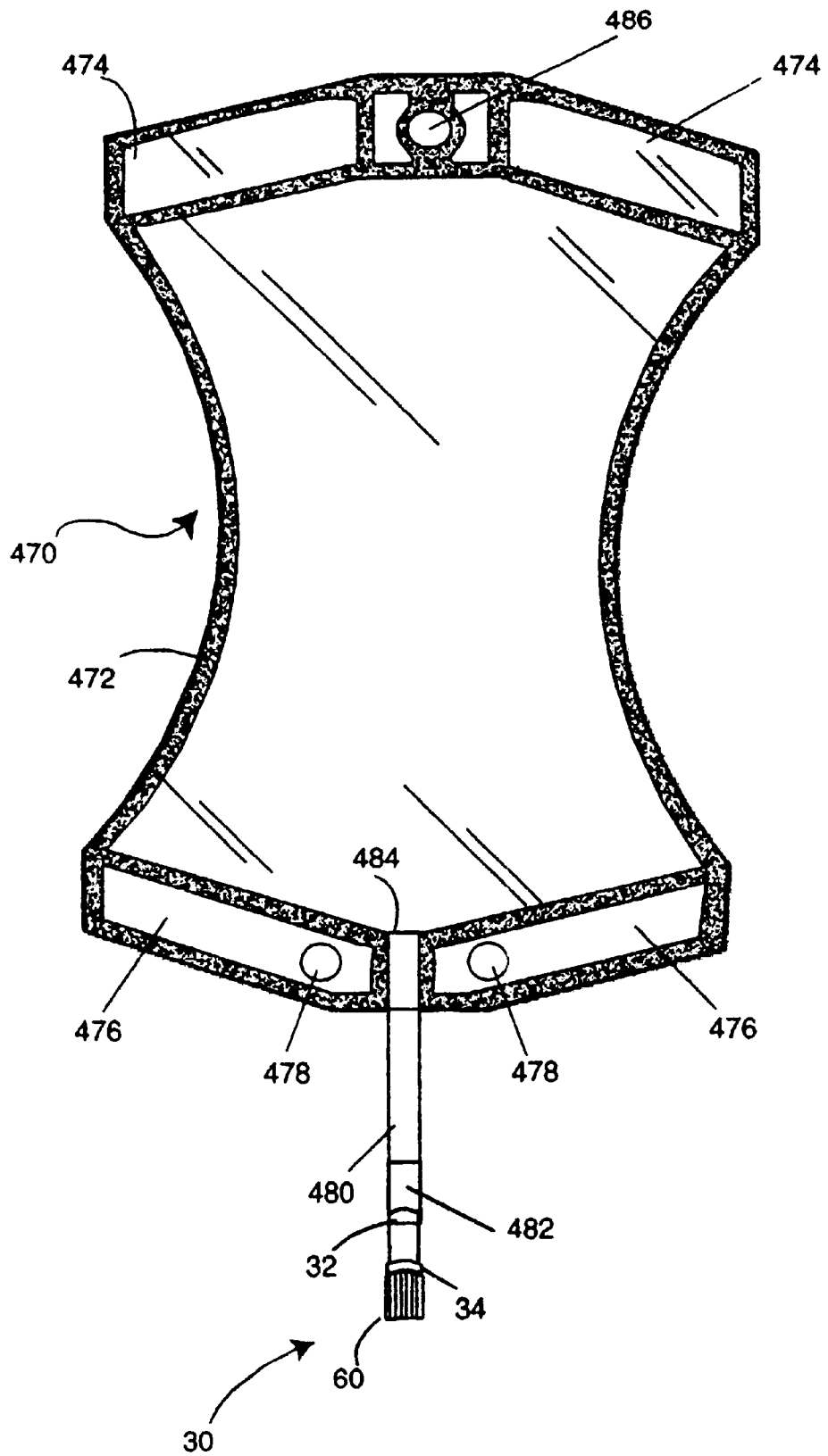
Figure 27:
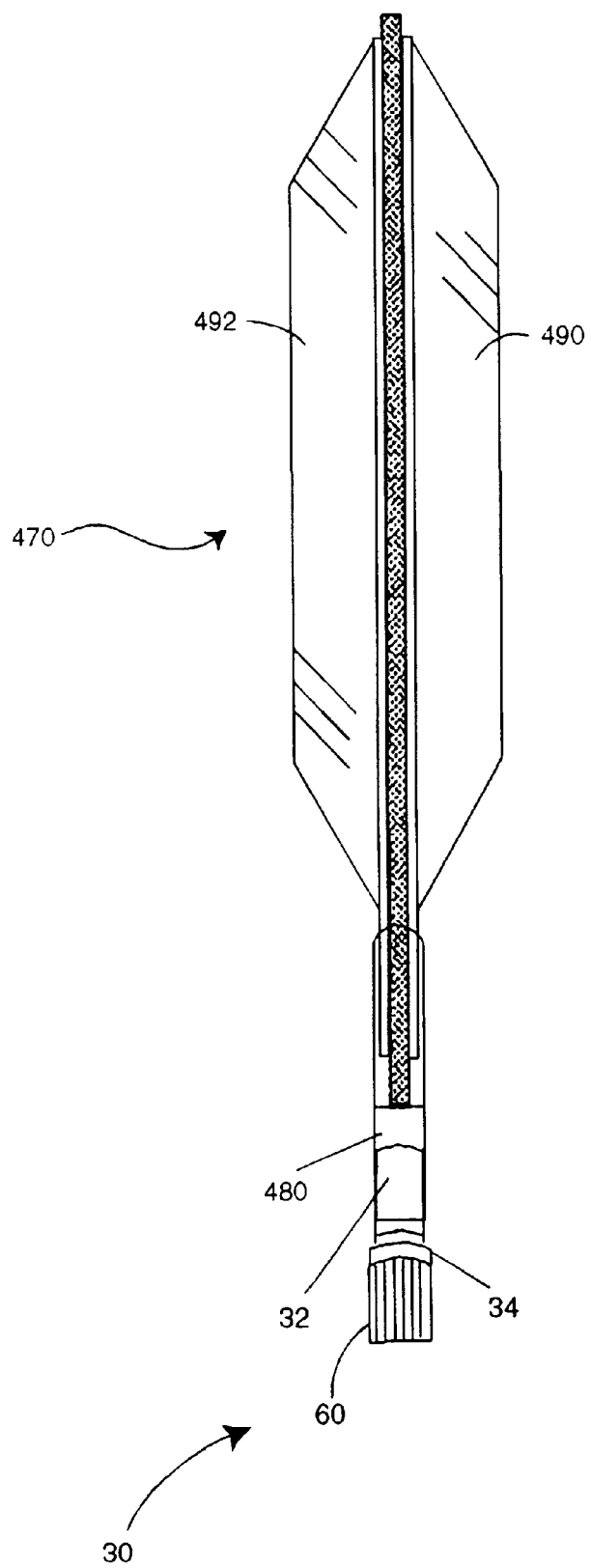
Figure 28:
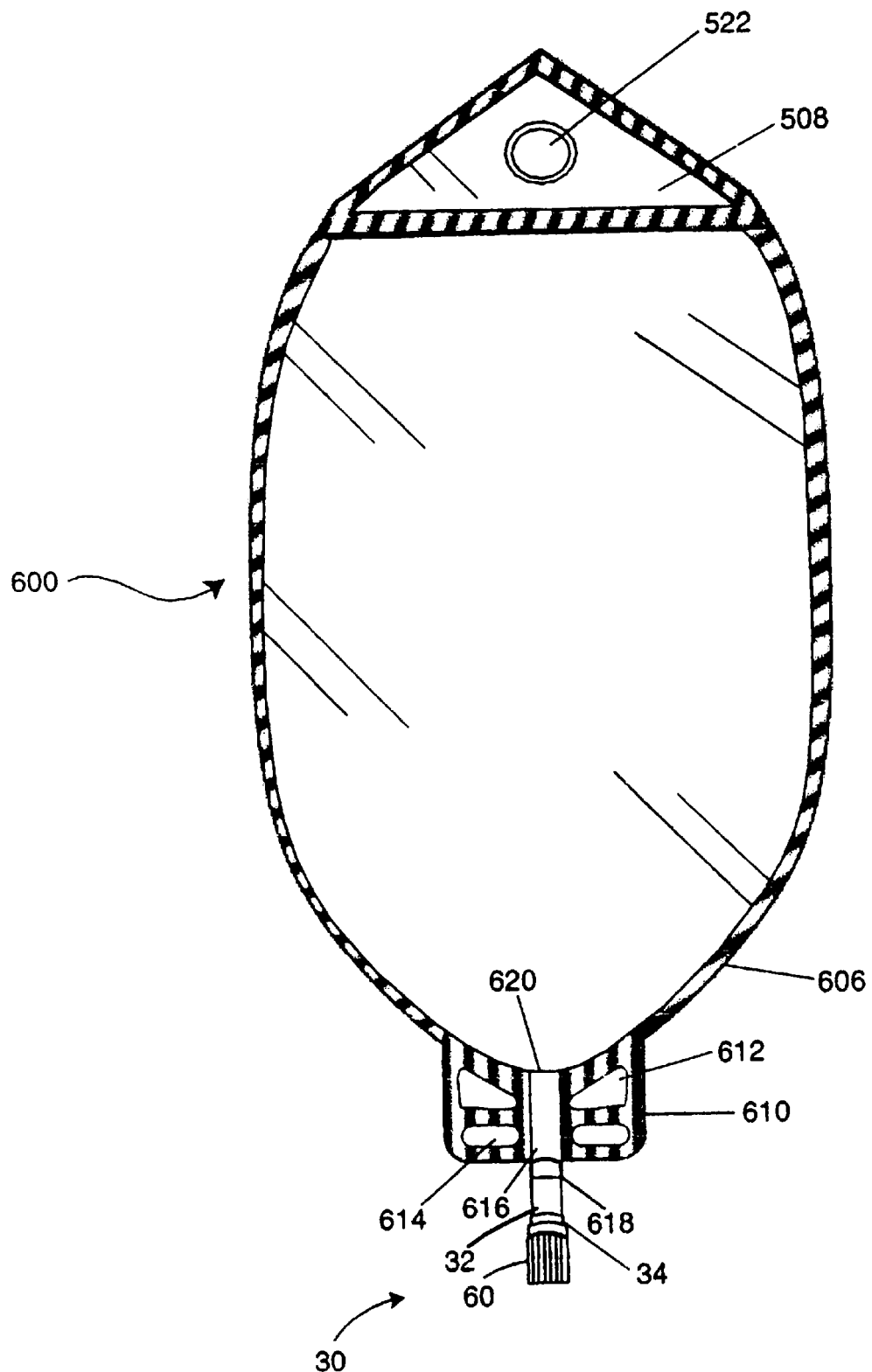
Figure 29:
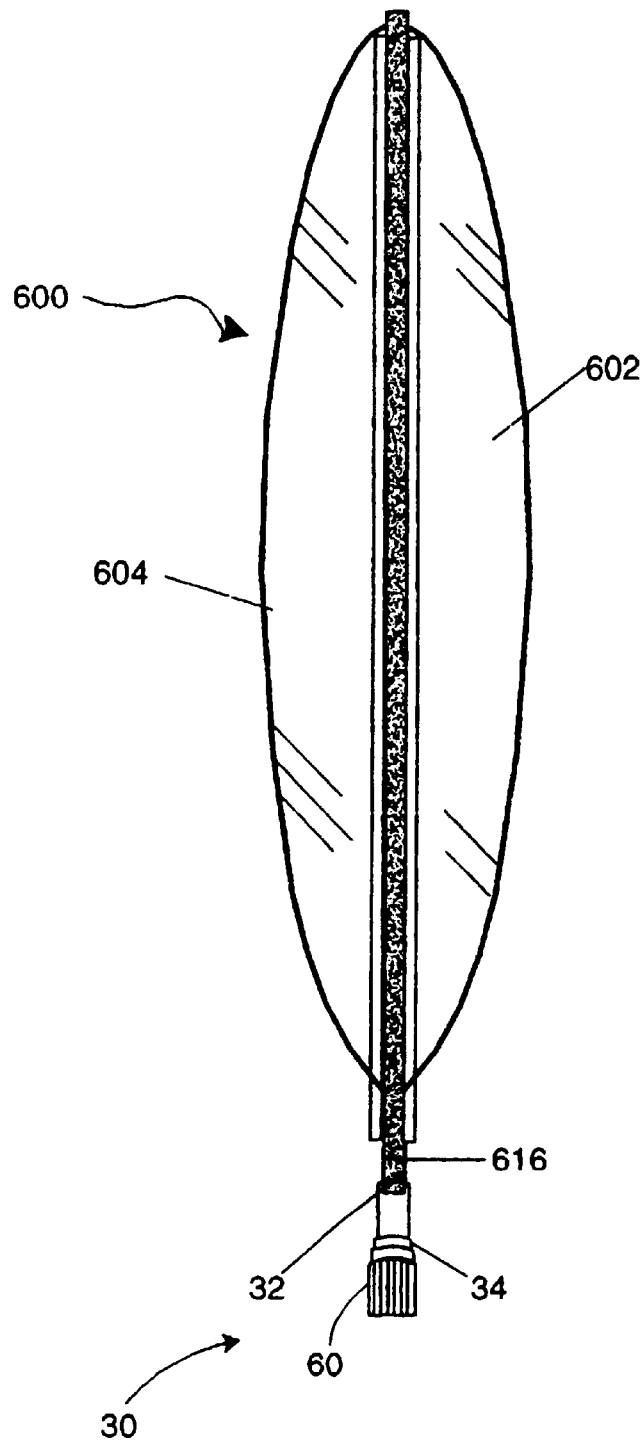
Figure 30:
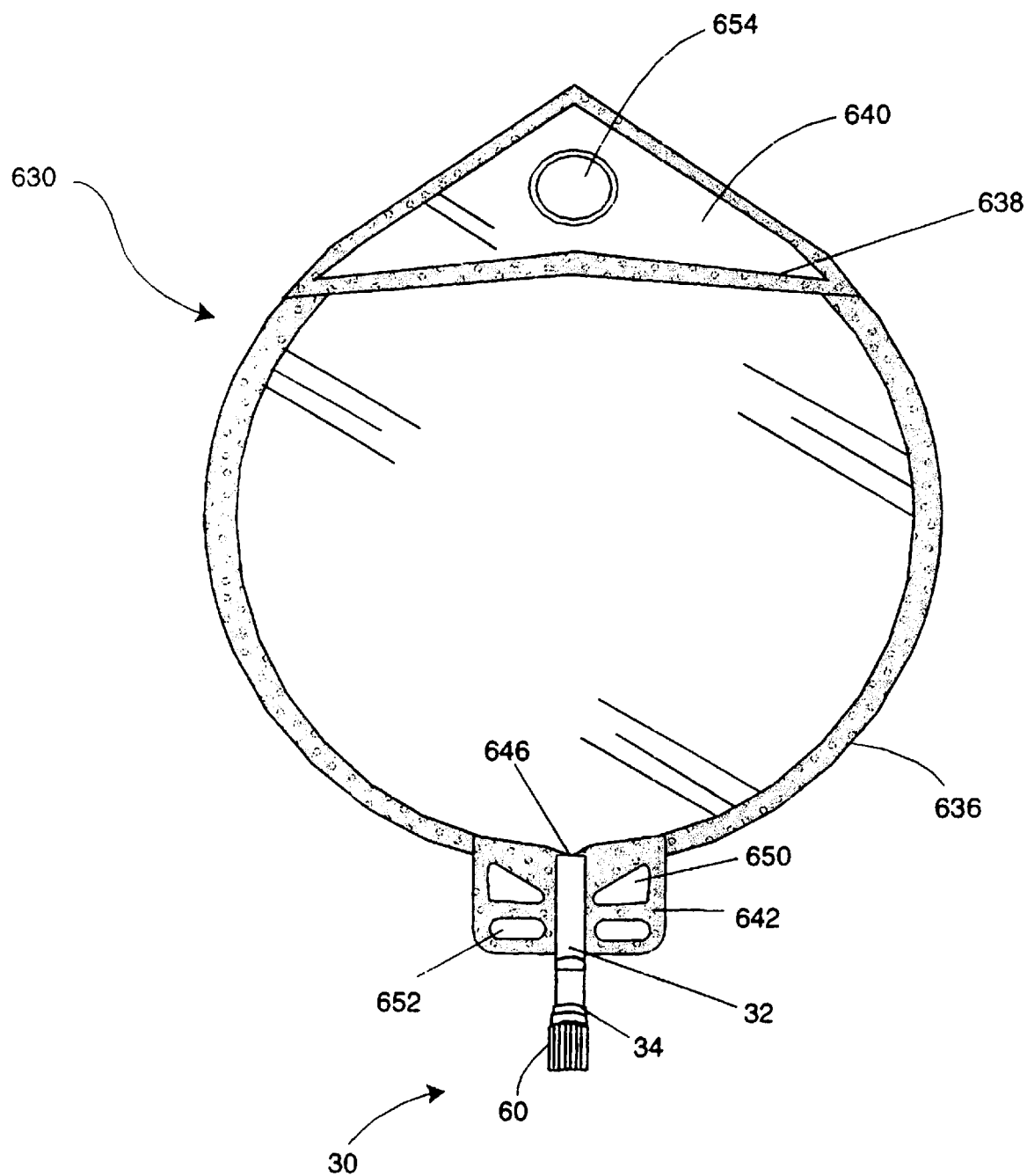
Figure 31:
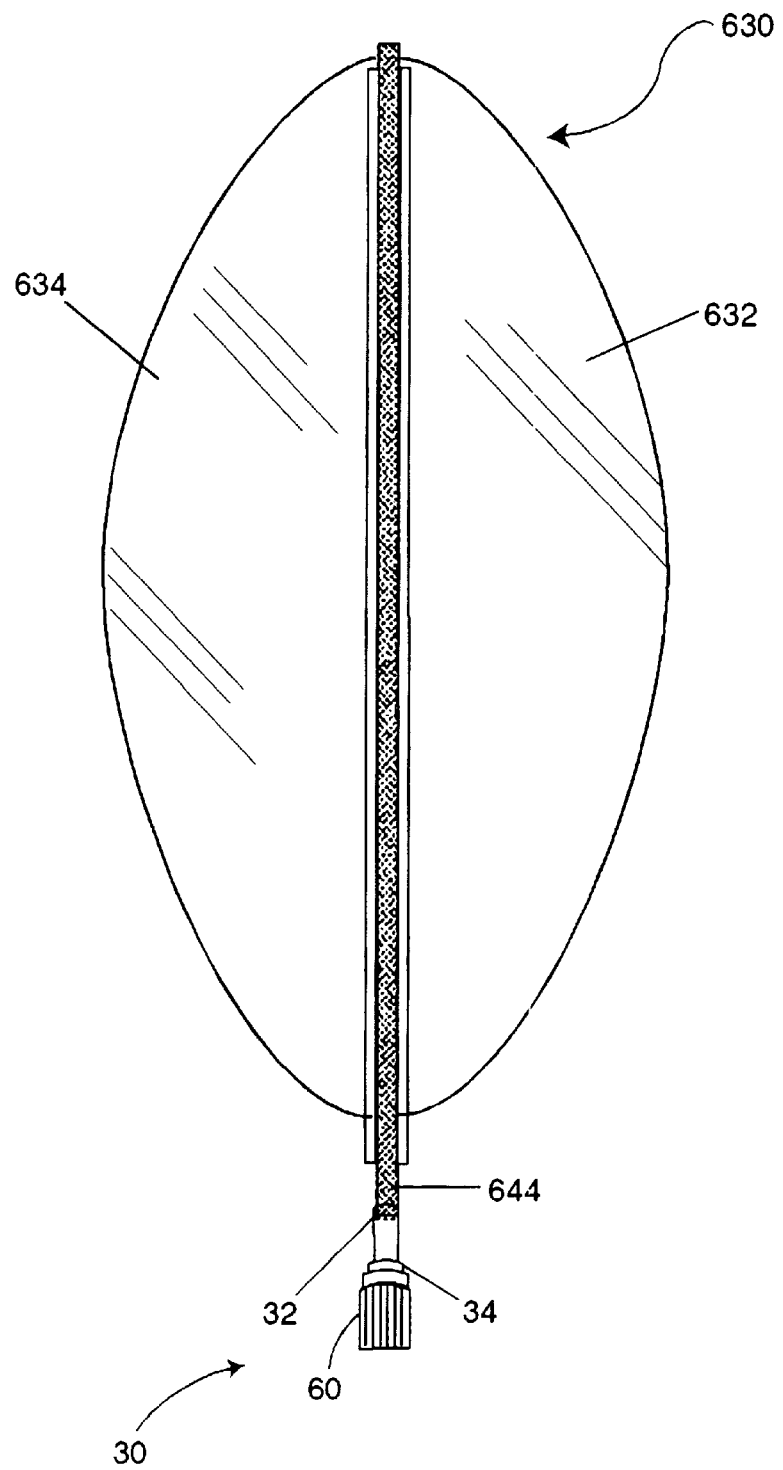

FIG. 22 is a front elevational view of a flexible unitary container of the present invention in the form of a generally rectangular pouch configuration, the back elevational view being identical with the front elevational view thereof;

FIG. 23 is a right-side elevational view of the flexible unitary container of FIG. 22, the left-side elevational view being identical with the right-side elevational view thereof, FIG. 24 is a front elevational view of another embodiment of the flexible unitary container of the present invention in the form of a generally hexagonal pouch configuration, the back elevational view being identical with the front elevational view thereof;

FIG. 25 is a right-side elevational view of the flexible unitary container of FIG. 24, the left-side elevational view being identical with the right-side elevational view thereof;

FIG. 26 is a front elevational view of another embodiment of the flexible unitary container of the present invention in the form of a generally parabolic pouch configuration, the back elevational view being identical with the front elevational view thereof;

FIG. 27 is a right-side elevational view of the flexible unitary container of FIG. 26, the left-side elevational view being identical with the right-side elevational view thereof;

FIG. 28 is a front elevational view of another embodiment of the flexible unitary container of the present invention in the form of a generally oval pouch configuration, the back elevational view being identical with the front elevational view thereof;

FIG. 29 is a right-side elevational view of the flexible unitary container of FIG. 28, the left-side elevational view being identical with the right-side elevational view thereof;

FIG. 30 is a front elevational view of another embodiment of the flexible unitary container of the present invention in the form of a generally spherical pouch configuration, the back elevational view being identical with the front elevational view thereof; and FIG. 31 is a right-side elevational view of the flexible unitary container of FIG. 30, the left-side elevational view being identical with the right-side elevational view thereof

DETAILED DESCRIPTION OF THE INVENTION

Referring To FIGS. 1, 2A, 2B, 2C and 2D, there is shown an intravenous bag 10 of conventional generally rectangular configuration made of inert, flexible, polymeric material, such as polyvinylchloride. The multiple use universal connector of the present invention will be described in reference to such flexible, polymeric bags, however, the multiple use universal connector can be used with other fluid containers such as bottles and vials of various configurations made of rigid or semi-rigid materials. Such containers will have fluid exit ports into which the universal connector can slideably be attached or it can be an integral part thereof The IV bag 10 contains a medical fluid 12 therein, such as therapeutic, diagnostic or nutritional preparation. The medical fluid 12 may be pre-sterilized in bulk prior to its transfer to the IV bag, or it may be sterilized in the IV bag using sterilizing equipment and techniques known in the art. The IV bag further comprises a fluid exit port or tube 14 the distal end 16 of which is in communication with medical fluid 12 and the proximal end 18 of which is to slideably receive distal end 32 of multiple use universal connector 30. Alternatively, multiple use universal connector 30 may be integral with fluid exit port or tube 14 of IV bag 10. On the proximal end 34 of multiple use universal connector 30, cap 60 is mounted having internal thread means thereon for enclosing said proximal end 34. Prior to use, cap 60 is removed from multiple use universal connector 30 for engagement with a luer connector.

FIG. 2A shows the multiple use universal connector without the cap; FIG. 2B shows the multiple use universal connector with the cap; and FIG. 2D shows the cap, all views being shown in perspective.

Reference is now being made to FIGS. 3A, 3B, 3C, 4A and 4B.

FIG. 3A shows a cross-sectional view of the multiple use universal connector without the cap taken along the line 3A—3A of FIG. 2A.

FIG. 3B shows the universal connector assembly taken along the line 3B—3B of FIG. 2B.

FIG. 3C shows a cross-section of the cap taken along the line 3D—3D of FIG. 2D, and FIG. 3D shows the top plan view thereof.

The multiple use universal connector 30 is of tube-like configuration comprising: distal end 32 and proximal end 34; inside wall 36 and outside wall 38. Integral part of outside wall 38 at the proximal end 34 thereof is positioned first cap-locking ring 40 spaced from second cap-locking ring 42. First cap-locking ring serves as a male thread to receive cap 60 and to engage its internal threads 66 and 66'; Second cap-locking ring 42 having proximal end 41 has a larger external diameter than the distance defined by a line connecting internal threads 66–66' located at the proximal end 68 of cap 60. Second cap locking-ring 42 serves as stopping means for cap 60 when cap 60 is threaded onto the multiple use universal connector 30.

Inside wall 36 of multiple use universal connector 30 comprises: a distal end 50 and proximal end 52. Distal end 50 is designed to slideably and sealingly engage fluid exit port or tube 14 to slide into the fluid exit port through its proximal end 18.

At the proximal end 52 of multiple use universal connector 30 a cylindrical opening is defined by side wall 54 and bottom wall 56. The cylindrical opening is designed to receive cylindrical protuberance defined by outside walls 78 and 80 of cap 60.

Bottom wall 56 and side wall 54 of cylindrical opening in multiple use universal connector 30, as best seen in FIG. 3B and FIG. 4A, contain an elastomeric diaphragm 90 bonded to the universal connector. The elastomeric diaphragm is of an M-shaped configuration and seals the fluid channel defined by the proximal end of inside wall 52 of universal connector 30. The diaphragm is of inert gas-impermeable polymeric material capable of flexing under internal or external pressures such as exerted during steam sterilization. The diaphragm has a durometer of from about 25 to about 80 Shore A. Suitable elastomeric materials for constructing the diaphragm include:

natural rubber;
acrylate-butadiene rubber;
cis-polybutadiene;
chlorobutyl rubber;
chlorinated polyethylene elastomers;
polyalkylene oxide polymers;
ethylene vinyl acetate;
fluorosilicone rubbers;
hexafluoropropylene-vinylidene fluoride-tetrafluoroethylene terpolymers, such as sold under the tradenames Fluorel and Viton;
butyl rubber;
polyisobutene, such as sold under the tradename Vistanex;
synthetic polyisoprene rubber;
silicone rubbers;
styrene-butadiene rubbers;
tetrafluoroethylene propylene copolymers; and
thermoplastic-copolyesters.

As best seen in FIGS. 4A and 4B, M-shaped diaphragm 90 comprises leg portion 92 and cup-shaped portion 94. Cup-shaped portion comprises:

a horizontal bottom portion 96; and
side portion 98 which enclose an obtuse angle between them. Leg portion 92 and side portion 98 typically have a thickness of from about 0.1 to 6 mm, while bottom portion 96 typically has a thickness of from about 1 to 20 mm.

The horizontal bottom portion 96 is provided with a slit 100 which extends from the top surface 102 of the horizontal bottom portion toward the bottom surface 104. However, the slit does not penetrate the bottom surface. The unpenetrated membrane, denoted by the numeral 106, is typically of from about 0.001 mm to about 2.0 mm. The unpenetrated membrane maintains the content of the container, in which the multiple use universal connector is used, in sealed condition. In use, when this membrane is ruptured by an external access means, such as a needle cannula, luer connector or spike, fluid communication is established between the content of the container and the external access means. Upon disengaging the external access means from the multiple use universal connector, the cup-shaped portion of the diaphragm reseals itself for the reason that the membrane is resilient and springs back to its original configuration. As a result, the container is resealed until the fluid withdrawal process is repeated.

As best seen in FIGS. 3C and 3D, cap 60 is designed for securely closing multiple use universal connector 30 at the proximal end 34 thereof, and protecting elastomeric diaphragm 90 from contact with the outside environment. The configuration of the cap closely approximates the luer connector shown in FIG. 6 which, in addition to the features detailed as the description of the cap proceeds, also contain a tubing conduit which is part of the luer connector. FIGS. 3C and 3D show cylindrical cap 60 comprising: outside wall 62 and inside wall 64. Outside wall 62 comprises: bottom wall 68; top wall 70; and central portion 72 of top wall 70. Inside wall 64 comprises: internal threads 66 and 66' extending towards the center of the cap; a cylindrical protuberance defined by outside wall 78 and bottom wall 80 extending distally into the space defined by the inside wall; and shoulder portion 82 connecting inside wall 64 and outside wall 78 of the cylindrical protuberance. In the proximal end of cap 60 there is located plug 71 defined by central portion 72 of top wall 70, and bottom wall 76. Plug 71 may be integral with the cap such as obtained by blow molding technique or the plug may be manufactured separately and subsequently sealed into the cap.

Referring again to FIGS. 3B and 3C, when cap 60 is threaded onto universal multiple use connector 30, bottom wall of protuberance 80 will be spaced from elastomeric diaphragm 90 allowing the membrane to flex outward under pressure, such as created during heat sterilization. However, spacing should not be more than about 0.1 to 3 mm so that under accidentally high pressures bursting of the membrane is prevented by the support of the bottom wall 80 of cylindrical protuberance.

FIGS. 5A, 5B and 5C show another embodiment of the multiple use universal connector of the present invention. FIG. 5A shows a cross-sectional view with the cap attached. FIG. 5B shows a cross-sectional view of an M-shaped diaphragm and FIG. 5C shows a top plan view thereof. In these figures the numbers with prime (') denote the same parts as in FIGS. 3A, 3B, 3C, 3D, 4A and 4B. In this embodiment the M-shaped diaphragm 90' comprises: leg portion 92'; and cup-shaped portion 94'. Cup-shaped portion comprises: horizontal bottom portion 96'; and side portion 98' which enclose a semi-circular surface 102'. Leg portion 92' and side portion 98' typically have a thickness of from about 0.1 to 6 mm, while bottom proton 96' typically have a thickness of from about 1 to 20 mm.

The horizontal bottom portion 96' is provided with slit 100' which extends from the top semi-circular surface 102' of the horizontal bottom portion toward the bottom surface 104. However, the slit does not penetrate the bottom surface. The unpenetrated membrane, denoted by the numeral 106' is typically of from about 0.001 mm to about 2.0 mm. The unpenetrated membrane maintains the content of the container, in which the multiple use universal connector is used, in sealed condition.

In use, when this membrane is ruptured by an external access means, such as a needle cannula, luer connector or spike, fluid communication is established between the content of the container and the external access means. Upon disengaging the external access means from the multiple use universal connector, the cup-shaped portion of the diaphragm reseals itself for the reason that the membrane is resilient and springs back to its original configuration. As a result, the container is resealed until the fluid withdrawal process is repeated.

We have found that both configurations of the M-shaped diaphragm perform well in resealing themselves in multiple use.

FIG. 6 shows in cross-sectional view a luer connector attachable to each of the embodiments of the present invention. The luer connector 120 comprises a cylindrical cap 130 and tubing conduit 150. Cylindrical cap 130 closely approximates cylindrical cap 60 of the multiple use universal connector shown in FIGS. 3B and 3C and its function is to be threaded onto the multiple use universal connector when fluid communication is desired. Prior to threading cylindrical cap 130 of luer connector 120 onto the multiple use universal connector 30, cylindrical cap 60 is removed and then replaced by cylindrical cap 130 of luer-connector 120.

Cylindrical cap 130 of luer connector 120 comprises outside wall 132 and inside wall 134. Outside wall 132 comprises: bottom wall portion 136; top wall portion 138; and central portion 140 of top wall portion 138. Inside wall 134 comprises: internal threads 142 and 142' extending towards the center of the cap.

Tubing conduit 150 is positioned in cylindrical cap 130 of luer connector 120 at its top central portion 140. Thickened outside wall portion 144 parallelly faces outside wall 152 of tubing conduit 150 and is permanently attached thereto by adhesive or other suitable means known in the art. Tubing conduit further comprises: inside wall of tubing conduit 154 forming a fluid channel 156; and bottom end portion of tubing conduit 158 which extends beyond bottom portion 136 of cylindrical cap 130 of luer connector. When threaded onto multiple use universal connector 30, luer connector 120 travels towards second cap-locking ring 142, contacts diaphragm membrane 90 or 90' with its bottom and portion 158 and exerts pressure thereon in a twisting motion. The exerted force ruptures the elastomeric membrane thereby allowing fluid communication between the luer connector 120 and the content of the intravenous infusion bag.

The multiple use universal connector 30 and 30' may also be used in containers, such as bottles and vials the contents of which are intended to be accessed by a hypodermic syringe having either a sharp or blunt cannula. When fluid withdrawal of fluid addition is desired, cylindrical cap 60 or 60' of multiple use universal connector 30 or 30' is removed and the diaphragm is pierced by the cannula providing access to the content of the container or its withdrawal therefrom.

FIG. 7A is a cross-section of the multiple use universal connector prior to penetration of the diaphragm by the luer connector of a syringe;

FIG. 7B is a cross-section of the multiple use universal connector at initial penetration and break-through of the diaphragm by the luer connector of a syringe;

FIG. 7C is a cross-section of the multiple use universal connector at complete penetration of the diaphragm by the luer connector whereby full flow access of the content of the container (not shown) is achieved; and FIG. 7D is a cross-section of the multiple use universal connector after removal of a luer connector whereby the diaphragm reseals itself.

The multiple use universal connector used in conjunction with the first embodiment of the present invention is shown in FIGS. 8 to 19.

Referring to FIGS. 8–11 there is shown a medical container contained in a generally bottle shape overwrap the combination of which is designated by the numeral 210. Medical container 212 is designed for the containment and delivery of diagnostic contrast media, nutrients and drug formulations. The medical container 212 comprises two superimposed sheets of suitable length and width made of flexible or pliable materials, such as polymeric materials including polyethylene, polypropylene, and preferably thermoplastic materials. The superimposed sheets forming the pouch-like container are made of transparent or at least translucent materials so as to allow observation of the amount of its content during the filling operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably flat welded to each other so as to form the pouch whose volume is zero before it is filled with a parenteral solution. When the medical container is filled or partially filled, it assumes the shape of a cushion. The superimposed sheets are joined together along marginal areas 214, 216, 218, 220, and 222. Access port 224 is located at the bottom portion of the medical container 212 and is sealed between the superimposed sheets. Access port 224 serves for both the filling and the delivery of a parenteral fluid. The access port 224 is closed with a cap 226 to maintain the content of the medical container sealed from the environment. In place of cap 226, access port 224 may be closed with universal connector 30. Alternatively, universal connector 30 may be integral with access port 224.

Medical container 212, as shown in FIG. 8, is enclosed by a bottle shape overwrap package 230. The overwrap package assume the configuration of the medical container 212 including access port 224 and cap 226. The walls of the overwrap package are slightly spaced from the walls of the medical container allowing just enough movement of the medical container within the overwrap package to cushion the medical container from the affects of environmental forces such as experienced on shipping or when the container/overwrap combination is dropped accidentally.

The overwrap package 230 comprises: two superimposed sheets of suitable length and width made of flexible or semi-rigid, transparent, polymeric materials including polyethylene, polypropylene and preferably thermoplastic materials so as to allow observation of the amount of the content of the medical container 212 and also to allow reading of identifying inscription on the medical container, such as the name, volume, manufacturer and lot number of the medical fluid. Each of the superimposed transparent sheets is preferably formed of laminated films at least one of which is impervious to atmospheric gases, moisture and bacteria. The superimposed sheet are joined together along marginal areas 232, 234, 238, and 240.

In order to maintain the integrity of content of light-sensitive medical fluids in the container the overwrap package 230 further comprises: opaque laminate films having UV barrier properties, such as metal foil, preferably aluminum, heat sealed and covering a substantial portion of the overwrap package 230. As shown in FIG. 8, bottom portion 250 extending toward access port 224, is provided with such an opaque laminate thereby protecting the integrity of light-sensitive medical fluids contained in the medical container.

Top portion 260 of overwrap package 230 is free of the opaque laminate so that the content of the medical container and inscription thereon can be viewed by healthcare professionals. While the transparent portion of the overwrap package is the top 20–30% of the total overwrap area as shown in FIG. 8, the ratio of transparent to opaque area may vary depending on the size of the medical container and the nature and volume of its content. The ratio of transparent to opaque areas are preferably 10:90, more preferably 20:80, and most preferably 30:70. Further, the transparent area may not only be on the top portion of the overwrap package as shown in FIG. 8, but also on any desired area, such as the bottom, side or mid portion of the overwrap package as long as the content of the medical container and certain important identifying inscriptions on the medical container can be viewed by health care personnel.

We have also found that the inside wall of overwrap package treated with silicone dioxide prevents fogging by condensation and thereby provides for better viewing of the medical container through its transparent portion.

Alternatively to the use of laminates having a metal foil layer to block UV rays from reaching the content of the medical container, certain transparent polymeric materials may be used for making the overwrap package 230.

FIGS. 12–15 show another embodiment of the present invention. The medical container and its overwrap are of rectangular configuration. Reference numerals with single superscript (') refer to this embodiment of the invention and the numerals will identify like parts referred to in FIGS. 8–11.

The process of making and the materials of construction are analogous to those described in reference to the embodiment in FIGS. 8–11. The difference being that in this embodiment the overwrap package 230 is of rectangular configuration unlike the bottle shape configuration of the first-described embodiment.

FIGS. 16–19 show still another embodiment of the present invention. The medical container and its overwrap are of rectangular configuration. Reference numerals with double subscript(") refer to this embodiment of the invention and the numerals will identify like parts as referred to in FIGS. 8–11 and 12–15. The distinguishing features of this embodiment from the embodiment shown in FIGS. 12–15 that in this embodiment the medical container 212" is sealed to the overwrap 230" at least at two points 231" and 233" spaced from each other. These seal points prevent sliding movement of the medical container 212 in its overwrap 230".

Materials of Construction of the Medical Container of the First Embodiment

The flexibly collapsible medical containers 12, 12' and 12" of the present invention are made of known polymeric materials having properties which make them suitable for sterile delivery of parenteral liquids. The sheets for forming the walls of the containers are preferably multilayer sheets and characterized by heat resistance, gloss, strength, flexibility, and chemical inertness. The sheets are transparent or at least translucent enabling visual inspection of the contents at all times during delivery of content from the container to the patient. The container must be sterilizable, preferably by heat, along with its content. At least one layer of the sheet must be impervious to atmospheric gases and to steam. Preferably, the internal surface of the containers in contact with the parenteral solution therein should be impervious to gas and steam. The interior layer in contact with the parenteral solution must not contain any toxic agents or even plasticizers which could leach out and contaminate the solution. The sheet may be made, for example, from polyvinylidene chloride sandwiched between two polyethylene or polyvinylacetate layers. The polyvinylidene chloride constitutes the impervious barrier. Further layers may be added to the face or back of the sheet, if desired, such as a polyolefin, preferably polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm$^2$; a moisture vapor transmission rate of about 14–20 (g/m$^2$/day at 38° C., 100% RH); and an oxygen barrier of 650 (cc/m$^2$/day at 23° C., 0% RH, bar. CRYOVAC ® sterilizable medical films (W. R. Grace and Co.) are especially suitable to construct the sheets used in the present invention. The films comprise a polyethylene layer sandwiched between polyester outer layers sealed together by a modified propylene copolymer. Typical properties of the film include: a thickness of about 190 micron; a tensile strength of about 250 kg/cm$^2$; a moisture vapor transmission rate of 5 (g/m$^2$/day at 38° C., 100% RH); and an oxygen barrier of about 1500 (cc/m$^2$/day at 23° C., 0% RH, bar).

Other polymeric films or sheets for constructing the flexible container of the present invention include: copolyester ether monolayer films, such as polycyclohexanedimethylcyclohexane, dicarboxylate elastomer made by Eastman Chemical Co.; and ethyl vinyl acetate made by Stedim, Inc. It is important that the fluid contacting layer of the multilayer sheet contain no plasticizer which may contaminate the fluid content of the container. Preferably, no plasticizer should be used at all on any of the multilayers to form the flexible container of the present invention.

Materials of Construction of the Overwrap Package

The overwrap package can be made of the same polymeric materials that the medical container is made of, except in its opaque portion to which, additionally, a UV barrier film is laminated which comprises a metallic foil, such as aluminum foil.

When, as previously indicated, the overwrap package is made of transparent UV rays barrier polymeric material, no UV barrier metallic foil is needed to be laminated to such UV rays barrier polymers.

In this embodiment the overwrap of the present invention at least a portion of which allows viewing the container within the overwrap is preferably made of a clear flexible film having UV absorbing (scavenging) or oxygen absorbing (scavenging) properties so that the content of the container is not affected by these environmental conditions. These polymers include in the form of a film alloys, blends, extrusions, laminations, surface modified and impregnated films or combinations thereof of the following polymeric materials which are capable to withstand autoclave or high-temperature sterilization and which contain UV absorbing or oxygen scavenging agent or into which such agents are incorporated by processes known to those skilled in the art:

copolyester elastomers,
ethylene methacrylate,
ethylene vinyl acetate,
ethylene vinyl alcohol,
low density polyethylene,
nylon/polypropylene,
polyester,
polyolefin,
polypropylene,
polyethylene, and
polyvinylchloride.

Blocking agents/UV stabilizers which may be included in the films include:

N-(2-Aminoethyl)-3-aminopropylmethyldimethoxy silane; 3-Aminopropylmethyldiethoxy silane: Amyitrichloroilane;

Bis (hydroxyethyl) aminopropyltriethoxy silane; Bis-(N-methylbenzanide) ethoxymethyl silane; Bis (trimethylsilyl)acetamide;

3-Chloroproplytriethoxysilane;

Di-t-butoxydiacetoxysilane;

Ethyltriacetoxysilane;

(3-Glycidoxypropyl)-methyldiethoxy silane;

Isobutyltrimethoxysilane; Isocyanatopropyltriethoxysilane;

3-Mercaptopropylmethyldimethoxysilane; Mercaptopropyltrimethoxysilane;

N-methylaminopropyltimethoxysilane; Methyltriacetoxysilane;

Methyltriethoxysilane; Methyltrimethoxysilane;

Octyltriethoxysilane;

2-Phenylethyltrichlorosilane; Phenyltriethoxysilane; n-Propyltrimethoxysilane 3-(N-Styrylmethyl-2-aminoethylamino) propyltrimethoxy silane hydrochloride, 2-(3'-t-butyl-2'-hydroxy-5'-methylphenyl)-5-chlorobenzotriazole, Bis (1,2,2,6,6,-pentamethyl-4-piperidinyl)3,5-di-butyl-4-hydroxybenzyl)butyl propanedioate and ethyl 2-cyano-3,3-diphenylacrylate.

Process of Making The Medical Container

The flexible plastic containers 212, 212', and 212" in the form of a bag, pouch or bottle are made of two rectangular sheets of polymeric materials flat welded together on four sides so as to define between the two sheets and the four welded sides a reservoir. The volume of the container is zero before it is filled and typically has an internal volume capacity of from about 50 to about 5,000 ml when it is filled with a medical fluid, such as a parenteral solution. Access ports 234, 234' and 234" are sealed by the same welding process used to seal the two superimposed layers of sheets together at the bottom center of the container. Upon completion of the welding process the container is suspended via holes 219, 219' and 219", followed by filling the container through the access port with the desired medical fluid. Alternatively, the container may be sealed by heat welding at its four edges except at its center portion and filled with the desired medical fluid prior to sealing the access port between the superimposed sheets. The container with the medical fluid therein is then autoclaved or sterilized by other methods of sterilization known in the art.

Process of Making The Overwrap Package

Subsequent to laminating the film layers together, the overwrap package is made by a heat welding process known in the art.

The multiple use universal connector used in conjunction with the second embodiment of the present invention is shown in FIGS. 20–22.

In this embodiment the present invention provides a flexible plastic container, in the shape of a bag or pouch, for the containment and delivery of diagnostic contrast media, nutrients and drug formulations. In the drawings where the reference character 310 in FIG. 20 indicates the container which, in a preferred embodiment, is a pouch-like device, comprises two superimposed sheets of suitable length and width made of flexible or pliable materials, such as polymeric materials including polyethylene, polypropylene, and preferably thermoplastic materials. The superimposed sheets forming the pouch-like container are preferably made of transparent materials so as to allow observation of the amount of its content prior to and subsequent to the filling, sterilization operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably mono or multilayer flat welded to each other so as to form the pouch whose volume is zero before it is filled with a parenteral solution. When the pouch is filled or partially filled, it assumes the shape of a small cushion. The superimposed sheets are joined together along marginal areas 328 and 330 as shown in FIG. 20.

Reference is no being made to the parts of the flexible container of the present invention using reference characters.

FIG. 20 shows the flexible container 310 sealed around its periphery 328 and 330 forming a reservoir or pouch for the containment of diagnostic contrast media, nutrients and drug formulations. The container has a top portion 312 and a bottom portion 314. Top portion 312 comprises marginal areas 334 and 326 sealed around their periphery and hole 316 at the center thereof for suspending the container when it is in use for delivering its content 340 to a delivery site.

The bottom portion 314 of container 310, defined by seal areas 344 and 342, terminates in first angle and second angle from the center thereof and relative to a horizontal plane crossing the center to direct and facilitate the flow of content contained in the container towards an access port. First and second angles are of from about 5° to about 45°, preferably from 10° to 30° and most preferably from 10° to 20°.

An access member or port 318 located at the center of the bottom portion of container 310 is sealed between the first sheet and second sheet of the container comprising a top, liquid-contacting portion and a bottom portion to which a flexible tubing, i.e., intravenous (IV) line may be fixedly attached by heat sealing or by any other means. Access member or port 318 serves for both the filling and for the delivery of the parenteral liquid. It is important that top portion of access member 318 is located below a horizontal plane crossing the center seal areas 344 and 342 so that all the liquid content of the container can be drained into flexible tubing of an IV line.

The bottom portion 314 further comprises marginal areas 320, 322, 330, 332 and 338 sealed around their periphery. These areas serve as reinforcements of the bottom portion 314.

A generally oval shaped reinforcing member or disc 350 is located inside the reservoir 340 approximately at the center thereof and attached by heat sealing or by other means to the inside wall of the reservoir as shown by seal lines 354 and 352 in FIG. 21.

Reinforcing member 350 is constructed from rigid polymeric material and comprises an oval shaped diskette narrowing at 356 and 358 towards the periphery 328 and 330 respectively, of reservoir 340; and ribs 360, 362 and 364 spanning the oval shaped diskette to insure that the oval shape of the diskette will not be deformed by the weight of the content of the reservoir. Ribs 360, 362 and 364 are spaced apart and along with the diskette define openings or holes allowing the liquid content to move freely towards the access member or port 318. While FIG. 21 shows three ribs 360, 362 and 364, it is to be noted that more than three ribs may be used to reinforce the diskette. Alternatively, if the diskette is sufficiently rigid to maintain its oval shape under the weight of the content of the reservoir, the diskette may be without the reinforcing ribs. It is also to be noted that more than one diskette may be used to keep the inside walls of the reservoir apart from each other so that no liquid droplets will be trapped between the walls when the content is being delivered.

Materials of Construction of the Second Embodiment

The flexible container of the present invention is made of known polymeric materials having properties which make them suitable for sterile delivery of parenteral liquids. The sheets for forming the walls of the container are monolayer, preferably multilayer, sheets and characterized by heat resistance, gloss, strength, flexibility, and chemical inertness. Preferably the sheets are transparent or at least translucent enabling visual inspection of the contents at all times during delivery of content from the container to the patient. The container must be sterilizable by dry heat, steam heat, irradiation (gamma), along with its content. At least one layer of the sheet provides a barrier to atmospheric gases and to steam. Preferably, the internal surface of the pouch in contact with the parenteral solution should be impervious to gases and steam. The interior layer in contact with the parenteral solution must not contain any toxic agents or even plasticizers which could leach out and contaminate the solution. The sheet may be made, for example, form polyvinyl chloride sandwiched between two polyethylene or polyvinylacetate layers. The polyvinyl chloride constitutes the impervious barrier. Further layers may be added to the face or back of the sheet, if desired, such as a polyolefin, preferably, polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm$^2$; a moisture vapor transmission rate of about 14–20 (g/m$^2$/day at 38° C, 100% RH); and an oxygen barrier of about 1500 (cc/m$^2$/day at 23° C., 0% RH, bar).

Other preferred polymeric films or sheets for constructing the flexible container of the present invention include: copolyester ether monolayer or multilayer films, manufactured from such as polycyclohexanedimethylcyclohexane dicarboxylate elastomer made by Eastman Chemical Co.; and ethyl vinyl acetate made by Stedim, Inc. It is important that the fluid contacting layer of the multilayer sheet contain no plasticizer which may contaminate the fluid content of the container. Preferably, no plasticizer should be used at all on any of the multilayers to form the flexible container of the present invention.

Access member or port as well as the oval shaped reinforcing disc and ribs may be made of polyvinylchloride which are sold commercially for use in medical devices. Other materials may also be used, such as CRYOVAC® Port Tubing (W. R. Grace & Co.) which comprise three concentric layers of polymeric materials: a polyolefin layer is sandwiched between an outer layer of modified propylene copolymer and an inner layer of ethylene vinyl acetate or polyvinyl chloride.

Process of Making The Container

The flexible plastic container in the form of a bag, pouch or bottle is made of two rectangular sheets of polymeric materials flat welded together on four sides so as to define between the two sheets and the four welded sides a reservoir. The container typically has an internal volume capacity of from about 50 to about 1,000 ml when it is filled with a medical fluid, such as a parenteral solution. The access member or port 318 is sealed by the same welding process used to seal the two superimposed layers of sheets together at the bottom center of the container 310.

Chronologically the process of making the container comprises the steps of:

a) pre-making the desired size of the reinforcing disc with or without the ribs by a method known in the art, such as blow molding;

b) cutting the desired size of rectangular sheets;

c) heat welding the reinforcing disc to one of the rectangular sheets followed by heat welding the other rectangular sheet to the disc; and d) welding together the rectangular sheets on four sides and simultaneously welding the access member or port into the bottom center portion of the container. Upon completion of the welding process the container is filled with the desired medical fluid and capped.

Alternatively, the container may be sealed by heat welding at its four edges except at is bottom center portion and filled with the desired medical fluid prior to sealing access member or port between the superimposed sheets. With either process, the container of the present invention, when filled with the desired medical fluid, provides for instant delivery requiring no assembly of the container and access member.

The multiple use universal connector used in conjunction with the third embodiment of the present invention is shown in FIGS. 22–31 wherein there are described A, B, C, D and E sub-embodiments based on configurational characteristics. In this third embodiment the present invention provides a flexible plastic container, in the form of a bag, pouch or bottle, for the containment and delivery of fluids, such as diagnostic contrast media, nutrients and drug formulations. The configuration of the flexible plastic container may be: polygon, such as rectangular, square, hexagonal and octagonal; spherical polygon; spheroidal; and ellipsoidal. Preferred configurations are rectangular, oval, hexagonal, parabolic and spherical.

In all the configurations of the third embodiment of the present invention shown in the drawings and/or referred to in the specification the flexible plastic container comprises two preformed sheets which are not coplanar and not parallel to each other. The sheets are superimposed on each other and sealed together at their periphery to form a reservoir for the containment of fluid. Contrary to prior art containers wherein flat, coplanar sheets are welded together at their periphery forming an essentially two dimensional reservoir prior to the introduction of a fluid thereinto, the flexible plastic container of the present invention is three dimensional prior to the introduction of fluid thereinto: each of the superimposed sheets is concavo-convex, the concave surface being towards the content of the reservoir while the convex surface faces towards the outside. Although being in a collapsed state, the container has, in addition to its length and width, a depth separating the two superimposed sheets. Upon filling the reservoir the container assumes the preformed shapes of the two non-coplanar concavo-convex sheets.

Third Embodiment A

Referring to the drawings, FIG. 22 shows in a front elevational view a generally rectangular, flexible, transparent plastic pouch generally designated at 410 partially filled with fluid 436. The pouch comprises at least one hole 417 for suspending when it is used for delivering its fluid content. In its filled or partially filled state, when suspended, the pouch assumes the shape of a small cushion: while in an unfilled and suspended state the three dimensional configuration of the pouch is less pronounced.

The flexible pouch 410 comprises preformed superimposed sheets joined together by heat sealing means along marginal areas 412, 414, 416, 418 and 420. Preferably the bottom portion of pouch 410 terminates in a first angle A and a second angle A' from the center C and relative to a horizontal plane crossing the center C of said bottom portion to direct and facilitate the flow of content 436 contained in the pouch towards an access port. Angles A and A' are of from about 5° to about 45°, preferable from 100 to 30°, and most preferably from 10° to 20°.

An access port 430 located at center C of the bottom portion of the pouch 410 is sealed between the first sheet and the second sheet of the pouch comprising a top, liquid-contacting portion 432 and a bottom portion 434 to which access means, such as an intravenous line can be permanently or fixedly attached by heat sealing or by other means. Access port 430 serves for both the filling and for the delivery of parenteral fluids, such as contrast media and drug formulations. Marginal area 416 comprises at least one hole 417 for suspending the pouch when used for delivering the content thereof to a delivery site. Marginal area 420 comprises at least one and preferably a plurality of holes 421 to facilitate suspending the pouch during the filling process.

FIG. 23 shows a right-side elevational view of the flexible plastic pouch shown in FIG. 22, the left-side elevational view being identical with the right-side elevational view thereof. As shown by the side elevational view the sheets 430 and 440 forming the pouch 410 are spaced from each other while the pouch is filled or partially filled with a fluid. The spacing of the sheets is less pronounced prior to the pouch being filled with a fluid.

Third Embodiment B

FIGS. 24 and 25 show a second embodiment of the flexible unitary container in the form of a generally hexagonal pouch configuration: FIG. 24 showing a front elevational view and FIG. 25 showing a right-side elevational view thereof. The back elevational view is substantially identical with the front elevational view, while the left-side elevational view is identical with the right-side elevational view.

The hexagonal pouch 440 comprises preformed superimposed sheets joined together by heat sealing means along marginal areas 442, 444, 446, 448 and 450. The bottom portion by the configuration of the hexagon directs the flow of fluid content 462 to access port 452 which is sealed between first sheet 454 and second sheet 456. Access port comprises top liquid contacting portion 458 and bottom portion 460. Access port 452 serves for both the filling and the delivery of fluids, such as contrast media and drug formulations. Marginal area 446 comprises at least one hole 447 for suspending the pouch when used for delivering the content thereof to a delivery site. Marginal area 450 comprises at least one and preferably a plurality of holes 451 to facilitate suspending the pouch during the filling process. A hexagonal logo 468 is optionally printed on the front or back or both sides of the pouch.

Third Embodiment C

FIG. 26 shows in a front elevational view of the third embodiment C of the flexible unitary container of the present invention in the form of a generally parabolic pouch configuration, the back elevational view being identical with the front elevational view thereof, and FIG. 27 shows a right-side elevational view of the pouch of FIG. 26, the left-side elevational view being identical with the right-side elevational view thereof.

The pouch 470 comprises preformed superimposed sheets 490 and 492 joined together by heat sealing means along marginal areas 472, 474 and 476. Fluid content flows toward access port 480, which is sealed between the superimposed sheets. Access port 480 comprises top liquid contacting portion 484 and bottom portion 482. The access port serves both for filling the pouch and delivering of fluids to a site. Marginal area 474 comprises at least one hole 486 for suspending the pouch when used for delivering the content thereof to a delivery site. Marginal area 476 comprises at least one and preferably a plurality of holes 478 to facilitate suspending the pouch during the filling process.

Third Embodiment D

FIG. 28 shows in a front elevational view a third embodiment D of the flexible unitary container of the present invention in the form of a generally oval or elliptical pouch configuration, the back elevational view being identical with the front elevational view thereof, and FIG. 29 shows a right-side elevational view of the pouch shown in FIG. 28, the left-side elevational view being identical with the right-side elevational view thereof.

The pouch 500 comprises preformed superimposed sheets 502 and 504 joined together by heat sealing means along marginal areas 506, 508 and 510. The bottom portion of the pouch is provided with an access port 516 which is sealed between the preformed superimposed sheets 502 and 504. Access port 516 comprises a top liquid contacting portion 520 and bottom portion 518. The access port serves for the filling and the delivery of fluids into and out of the pouch. Marginal area 510 comprises at least one and preferably a plurality of holes 512 and 514 to facilitate suspending the pouch during the filling process. Marginal area 508 comprises at least one hole 522 for suspending the pouch when it is used for delivering the content thereof to a delivery sight.

Third Embodiment E

FIG. 30 shows in a front elevational view the third embodiment E of the flexible unitary container of the present invention in the form of a generally spherical pouch configuration, the back elevational view being identical with the front elevational view thereof, and FIG. 31 shows a right-side elevational view of the pouch shown in FIG. 30, the left-side elevational view being identical with the right-side elevational view thereof.

The pouch 530 comprises preformed superimposed sheets 532 and 534 joined together by heat sealing means along marginal areas 536, 538, 540 and 542. The bottom portion of the pouch is provided with an access port 544 which is sealed between the preformed superimposed sheets 532 and 534. Access port 544 comprises a top liquid contacting portion 546 and bottom portion 548. The access port serves for both the filling and delivery of fluids into and out of the pouch. Marginal area 542 comprises at least one and preferably a plurality of holes 550 and 552 to facilitate suspending the pouch during the filling process. Marginal area 540 comprises at least one hole 554 for suspending the pouch when it is used for delivering the content thereof to a delivery site.

Materials of Construction of the Third Embodiment

The flexible container of the present invention is made of known polymeric materials having properties which make them suitable for sterile delivery of parenteral liquids. The sheets for forming the walls of the container are preferably multilayer sheets and characterized by heat resistance, gloss, strength, flexibility, and chemical inertness. Preferably the sheets are transparent or at least translucent enabling visual inspection of the contents at all time during the delivery of content from the container to the patient. The container must be sterilizable, preferably by heat, along with its content. At least one layer of the sheet must be impervious to atmospheric gases and to steam. Preferably, the internal surface of the pouch in contact with the parenteral solution should be impervious to gases and steam. The interior layer in contact with the parenteral solution must not contain any toxic agents or even plasticizers which could leach out and contaminate the solution. The sheet may be made, for example, from polyvinylidene chloride sandwiched between two polyethylene or polyvinylidene layers. The polyvinylidene chloride constitutes the impervious barrier. Further layers may be added to the face or back of the sheet, if desired, such as a polyolefin, preferably, polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm$^2$; a moisture vapor transmission rate of about 14–20 (g/m$^2$/day at 38° C., 100% RH); and an oxygen barrier of 650 (cc/m$^2$/day at 23° C., 0% RH, bar. CRYOVAC ® sterilizable medical films (W.R. Grace and Co.) are especially suitable to construct the sheets used in the present invention. The films comprise a polyethylene layer sandwiched between polyester outer layers sealed together by a modified propylene copolymer. Typical properties of the film include: a thickness of about 190 micron; a tensile strength of about 250 kg/cm$^2$, a moisture vapor transmission rate of 5 (g/m$^2$/day at 38° C., 100% RH); and an oxygen barrier of about 1500 (cc/m$^2$/day at 23° C., 0% RH, bar).

Other preferred polymeric films or sheets for constructing the flexible container of the present invention include: copolyester ether monolayer films, such as polycyclohexanedimethylcyclohexane dicarboxylate elastomer made by Eastman Chem. Co.; and ethyl vinyl acetate made by Stedim, Inc. It is important that the fluid contacting layer of the multilayer sheet contain no plasticizer which may contaminate the fluid content of the container. Preferably, no plasticizer should be used at all on any of the multilayers to form a flexible container of the present invention.

The Process of Making the Third Embodiment of the Present Invention

The manufacturing process of making the flexible container comprises the steps of:

forming thermoplastic sheets into desired three dimensional shapes; and heat sealing the marginal areas to form the container.

The thermoplastic sheets of single or multi-layered films are optionally pre-heated to a pliable state and placed over cavities which were pre-made to desired shapes, such as square, rectangular, spherical and the like. The cavities are made of steel or other suitable material. The pre-heating may be accomplished by using various techniques known in the art, such as blowing hot air over the sheets or drawing the sheets across a heated platen or bar. The cavity used may be a male or female cavity equipped with small holes through which vacuum can be applied. In either case the cavity has one half of the desired shape of the finished container. A series of these halves are then superimposed and sealed together at their marginal areas to form the container.

The pre-heated sheet is fed over the top surface of the cavity and heated to a temperature at which it softens and is able to flow into the cavity. As the vacuum is applied, air between the wall of the cavity and the soft, flowable sheet is exhausted causing the sheet to be drawn into the cavity and conform to the cavity's configuration. The so-formed three dimensional sheet is then allowed to cool to a temperature at which it no longer flows and is removed from the cavity.

Alternatively the preformed sheets may be produced by using both a male and female configuration cavity, the female cavity being provided with a plurality of small holes connected to a vacuum source. The thermoplastic sheet is heated and simultaneously pulled into the female cavity and pushed by the male cavity having a smaller dimension. Vacuum is then applied to the female cavity to exhaust any air that might be trapped between the sheet and the surface of the female cavity. Still more alternatively, the male cavity may be provided with a plurality of holes through which air can be supplied forcing the thermoplastic sheet into the female cavity to assume its configuration.

In a still further alternative process thermoplastic material is placed in a mold having a desired configuration, heated past its softening point, and applying pressurized gas to expand the thermoplastic material to assume the configuration of the mold. The thickness of the finished product can be controlled by the amount of thermoplastic material placed in the mold.

Subsequent to forming a series of three dimensional halves, two symmetrical halves are superimposed on each other and heat and pressure are applied to their marginal areas to fuse the two halves together to form a hermetic seal between them. One ore more exit ports are introduced between the two halves of the container during the joining process for providing access to fill or empty the container. Desirably, holes are punched into the top and bottom perimeter areas of the container to facilitate suspension of the container for filling or delivering its content.

| LIST OF REFERENCE NUMBERS USED |  |
|---|---|
| MULTIPLE USE UNIVERSAL CONNECTOR | |
| Intravenous infusion bag (IV) bag | 10 |
| Fluid contained in bag | 12 |
| Fluid exit port or tube in IV bag | 14 |
| Distal end of fluid exit port or tube | 16 |

-continued

LIST OF REFERENCE NUMBERS USED

MULTIPLE USE UNIVERSAL CONNECTOR

| | |
|---|---|
| Proximal end of fluid exit port or tube | 18 |
| Bottom seam of IV bag | 20 |
| Multiple use universal connector | 30,30' |
| Distal end of multiple use universal connector | 32,32' |
| Proximal end of multiple use universal connector | 34 |
| Inside wall of multiple use universal connector | 36 |
| Outside wall of multiple use universal connector | 38 |
| First cap-locking ring | 40,40' |
| Proximal end of second cap locking-ring | 41,41' |
| Second cap-locking ring | 42 |
| Distal end of inside wall of multiple use universal connector | 50 |
| Proximal end of inside wall of multiple use universal connector | 52,52' |
| Side wall of cylindrical opening at proximal end of multiple use universal connector | 54 |
| Bottom wall of cylindrical opening at proximal end of multiple use universal connector | 56 |
| Cylindrical cap of multiple use universal connector | 60,60' |
| Internal threads on cap | 66,66' |
| Bottom wall of cap | 68,68' |
| Top wall of cap | 70 |
| Plug | 71 |
| Central portion of top wall | 72 |
| Side wall of plug | 74 |
| Bottom wall of plug | 76 |
| Outside wall of cylindrical protuberance of cap | 78 |
| Bottom wall of cylindrical protuberance of cap | 80 |
| Shoulder connecting inside wall of cap and outside wall of cylindrical protuberance of cap | 82 |
| M-shaped diaphragm | 90,90' |
| Leg portion of M-shaped diaphragm | 92,92' |
| Cup-shaped portion of M-shaped diaphragm | 94,94' |
| Horizontal bottom portion of cup-shaped portion | 96 |
| Side portion of cup-shaped bottom | 98,98' |
| Slit in bottom portion | 100,100' |
| Top surface of horizontal bottom portion | 102 |
| Bottom surface of horizontal bottom portion | 104 |
| Unpenetrated membrane | 106,106' |
| Luer connector | 120 |
| Cylindrical cap of luer connector | 130 |
| Top portion of cylindrical cap | 138 |
| Center top portion of cylindrical cap | 140 |
| Wall portion of cylindrical cap facing tubing conduit 150 | 144 |
| Tubing conduit in luer connector | 150 |
| Outside wall of tubing conduit | 152 |
| Inside wall of tubing conduit | 154 |
| Fluid channel | 156 |
| Bottom end portion of tubing conduit | 158 |
| First Embodiment | |
| Bottle shape overwrap | 210,230, 230', 230" |
| Medical container | 212,212', 212" |
| Marginal areas of superimposed sheets of container | 214,216, 218,220 and 222 |
| Access port | 224 |
| Cap closing the access port | 226 |
| Marginal areas of superimposed sheets of overwrap | 231",232, 233", 234,234', 234", 238 and 240 |
| Bottom portion of overwrap | 250 |
| Top portion of overwrap | 260 |
| Holes | 219,219', 219" |
| Second Embodiment | |
| Container | 310 |
| Marginal areas of superimposed sheets | 328,330 |
| Top portion of container | 312 |
| Bottom portion of container | 314 |
| Marginal areas of bottom portion | 320,322, 332 and 338 |
| Marginal areas of top portion | 326,334 |
| Hole in top portion of marginal area | 316 |
| Container, reservoir | 340 |
| Bottom portion of seal areas of container | 344,342 |
| Port or access member | 318 |
| Reinforcing member or disc | 350 |
| Narrowed portion of disc | 356,358 |
| Ribs in disc | 360,362, 364 |
| Third Embodiment | |
| A) | |
| Rectangular pouch | 410 |
| Fluid in pouch | 436 |
| Hole for suspending pouch | 417 |
| Marginal areas of superimposed sheets | 412,414, 416,418 and 420 |
| Access port | 430 |
| Top portion of access port | 432 |
| Bottom portion of access port | 434 |
| B) | |
| Hexagonal pouch | 440 |
| Marginal areas of superimposed sheets | 442,444, 446,448 and 450 |
| Fluid content of pouch | 462 |
| Access port | 452 |
| First sheet | 454 |
| Second sheet | 456 |
| Top portion of access port | 458 |
| Bottom portion of access port | 460 |
| Hole for suspending pouch for delivering fluid | 447 |
| Hole for suspending pouch for filling the pouch | 451 |
| Hexagonal logo | 468 |
| C) | |
| Parabolic pouch | 470 |
| Superimposed sheets | 490 and 492 |
| Marginal areas | 472,474 and 476 |
| Access port | 480 |
| Top portion of access port | 484 |
| Bottom portion of access port | 482 |
| Hole for suspending pouch for delivering fluid | 486 |
| Hole for suspending pouch for filling the pouch | 478 |
| D) | |
| Oval/elliptical pouch | 500 |
| Superimposed sheets | 502 and 504 |
| Marginal areas | 506,508 and 510 |
| Access port | 516 |
| Top portion of access port | 520 |
| Bottom portion of access port | 518 |
| Hole for suspending pouch for delivering fluid | 512 and 514 |
| Role for suspending pouch for filling the pouch | 522 |
| E) | |
| Spherical pouch | 530 |
| Superimposed sheets | 532 and 534 |
| Marginal areas | 536,538, 540 and 542 |
| Access port | 544 |
| Top portion of access port | 546 |

-continued

LIST OF REFERENCE NUMBERS USED

MULTIPLE USE UNIVERSAL CONNECTOR

| | |
|---|---|
| Bottom portion of access port | 548 |
| Hole for suspending pouch for delivering fluid | 550 and 552 |
| Hole for suspending pouch for filling the pouch | 554 |

Various modifications of the several embodiments disclosed will become apparent to those skilled in the art. The invention is intended to include such modifications to be limited only by the scope of the claims.

What is claimed is:

1. A multiple use universal connector and flexible medical container assembly containing a light-sensitive medical fluid therein packaged in an overwrap to prevent degradation of said light-sensitive medical fluid wherein:

(a) said flexible medical container comprises:
first and second transparent polymeric sheets superimposed and sealed together at their periphery defining an interior reservoir for the containment of said light-sensitive medical fluid, said flexible medical container having an inside wall, an outside wall, a top portion and a bottom portion;
an access port located at the bottom portion sealed between said first and second transparent polymeric sheets;

(b) a multiple use universal connector sealed into said access port, said multiple use universal connector comprising:
(1) a connector body of tube-like configuration having a distal end and a proximal end, said distal end being slideably inserted into said access port of said flexible medical container and said proximal end sealing the light-sensitive medical fluid in said flexible medical container by an
(2) elastomeric diaphragm and a
(3) removable cap;
(4) a first cap-locking ring on the proximal end of said connector body which serves as a male thread to receive said removable cap; and
(5) a second cap-locking ring, spaced from said first cap-locking ring towards the distal end of said connector body, which serves as stopping means for the removable cap when the removable cap is threaded onto the connector body;
said elastomeric diaphragm is of M-shaped configuration, capable of flexing under pressure sealing said proximal end of said connector body, and being capable of re-sealing itself after being pierced by an external access means; and
said removable cap being threaded onto the proximal end of said connector body to protect said elastomeric diaphragm from environmental forces to maintain said diaphragam in aseptic condition prior to removal of said removable cap for accessing the light-sensitive medical fluid of the flexible medical container or transferring a light-sensitive medical fluid to said flexible medical container by an external access means;
said flexible medical container and said multiple use universal connector assembly being enclosed in an overwrap, (c) said overwrap comprises:
first and second tarnapartent UV rays barrier polymeric sheets with an inside wall and an outside wall having a square, round oval, hexagonal, octagonal or rectangualr configuration superimposed and sealed together at their periphery hermetically sealing said flexible medical container and said universal connector assembly preventing penetration of UV rays into the light-sensitive medical fluid container in said flexible medical container.

2. The multiple use universal connector and flexible medical container assembly of claim 1 wherein: said first and second transparent polymeric sheets superimposed and sealed together at their periphery define an interior reservoir having a configuration selected from the group consisting of square, round, oval, hexagonal, octagonal and rectangular; and said first and second transparent UV rays barrier polymeric sheets superimposed and sealed together at their periphery define said overwrap having a configuration selected from the group consisting of square, round, oval, hexagonal, octagonal and rectangular.

3. The multiple use universal connector and flexible medical container assembly packaged in an overwrap of claim 1 wherein said first and second transparent polymeric sheets defining said interior reservoir are made of polyvinylidene chloride sandwiched between two layers of polyethylene or polyvinylacetate.

4. The multiple use universal connector and flexible medical container assembly packaged in an overwrap of claim 1 wherein the inside wall of said overwrap is treated with silicone dioxide to prevent fogging by condensation.

5. The multiple use universal connector and flexible medical container assembly packaged in an overwrap of claim 1 wherein the inside wall of said overwrap is spaced from the outside wall of said flexible medical container to allow for slight cushioning movement of said flexible medical container within said overwrap.

6. The multiple use universal connector and flexible medical container assembly packaged in an overwrap of claim 1 wherein said flexible medical container is sealed to said overwrap at least at two contact points to prevent excessive sliding movement of said flexible medical container in said overwrap.

7. The multiple use universal connector and flexible medical container assembly packaged in an overwrap of claim 1 wherein said elastomeric diagphragm has a thickness of from about 0.001 mm to about 2.0 mm and a durometer of from about 25 to about 80 Shore A.

8. The multiple use universal connector and flexible medical container assembly packaged in an overwrap of claim 1 wherein said elastomeric diaphragm is of an elastomeric material selected from the group consisting of:

natural rubber;
acrylate-butadiene rubber;
cis-polybutadiene;
chlorobutyl rubber;
chlorinated polyethylene elastomers;
polyalkylene oxide polymers;
ethylene vinyl acetate;
fluorosilicone rubbers;
hexafluoropropylene-vinylidene fluoride-tetrafluoroethylene terpolymers;
butyl rubber;
polyisobutene;
synthetic polyisoprene rubber;
silicone rubbers;
styrene-butadiene rubbers;

tetrafluoroethylene propylene copolymers; and thermoplastic-copolyesters.

9. The multiple use universal connector and flexible medical container assembly packaged in an overwrap of claim 1 wherein said M-shaped diaphragm comprises: a leg portion and a cup-shaped portion wherein said cup-shaped portion is oriented toward the distal end of said universal connector.

10. The multiple use universal connector and flexible medical container assembly packaged in an overwrap of claim 9 wherein said cup-shaped portion comprises: a horizontal portion and a side portion which enclose an obtuse angle between them, said horizontal portion having a top surface and a bottom surface.

11. The multiple use universal connector and flexible medical container assembly packaged in an overwrap of claim 10 wherein said horizontal portion comprises a slit extending from the top surface thereof toward the bottom surface thereof leaving an unpenetrated portion in said bottom surface.

12. The multiple use universal connector and flexible medical container assembly packaged in an overwrap of claim 11 wherein said unpenetrated portion has a thickness of from about 0.001 mm to 2.0 mm.

13. The multiple use universal connector and flexible medical container assembly packaged in an overwrap of claim 9 wherein said cup-shaped portion comprises: a horizontal portion and a side portion which enclose a semi-circular surface between them said horizontal portion having a top surface and a bottom surface.

14. The multiple use universal connector and flexible medical container assembly packaged in an overwrap of claim 13 wherein said horizontal portion comprises a slit extending from the top surface thereof toward the bottom surface thereof leaving an unpenetrated portion in said bottom surface.

15. The multiple use universal connector and flexible medical container assembly packaged in an overwrap of claim 14 wherein said unpenetrated portion has a thickness of from about 0.001 mm to about 2.0 mm.

16. The multiple use universal connector and flexible medical container assembly packaged in an overwrap of claim 1 wherein said diaphragm reseals itself after puncture by a an external access means.

17. The multiple use universal connector and flexible medical container assembly packaged in an overwrap of claim 1 wherein said external access means comprises a luer connector or a syringe having a sharp or blunt needle cannula.

18. The multiple use universal connector and flexible medical container assembly packaged in an overwrap of claim 1 wherein said light-sensitive medical fluid is a therapeutic liquid.

19. The multiple use universal connector and flexible medical container assembly packaged in an overwrap of claim 1 wherein said light-sensitive medical fluid is a diagnostic media.

20. The multiple use universal connector and flexible medical container assembly packaged in an overwrap of claim 1 wherein said light-sensitive medical fluid is a nutritional liquid.

* * * * *